(12) United States Patent
Miyashita et al.

(10) Patent No.: US 12,097,144 B2
(45) Date of Patent: Sep. 24, 2024

(54) HEATING BODY AND METHOD FOR PRODUCING THE SAME

(71) Applicants: FERRIC INC., Tokyo (JP); S.T. CORPORATION, Tokyo (JP)

(72) Inventors: Eiji Miyashita, Tokyo (JP); Hirokazu Miyashita, Tokyo (JP); Hitoshi Usui, Tochigi (JP); Mitsuhiro Sakamoto, Tochigi (JP)

(73) Assignees: FERRIC INC., Tokyo (JP); S.T. CORPORATION, Tokyo (JP)

( * ) Notice: Subject to any disclaimer, the term of this patent is extended or adjusted under 35 U.S.C. 154(b) by 1127 days.

(21) Appl. No.: 16/622,511

(22) PCT Filed: Jun. 14, 2018

(86) PCT No.: PCT/JP2018/022742
§ 371 (c)(1),
(2) Date: Feb. 22, 2021

(87) PCT Pub. No.: WO2018/230651
PCT Pub. Date: Dec. 20, 2018

(65) Prior Publication Data
US 2022/0000658 A1 Jan. 6, 2022

(30) Foreign Application Priority Data
Jun. 15, 2017 (JP) ................... 2017-117578

(51) Int. Cl.
*A61F 7/03* (2006.01)
*A61F 7/00* (2006.01)
*A61F 7/02* (2006.01)

(52) U.S. Cl.
CPC ...... *A61F 7/034* (2013.01); *A61F 2007/0037* (2013.01); *A61F 2007/0223* (2013.01); *A61F 2007/0228* (2013.01)

(58) Field of Classification Search
CPC ...... A61F 2007/0037; A61F 2007/0204; A61F 2007/0206; A61F 2007/0214;
(Continued)

(56) References Cited

U.S. PATENT DOCUMENTS

| 2008/0289616 A1* | 11/2008 | Ohnishi | A61F 7/034 |
| | | | 126/263.01 |
| 2011/0130814 A1* | 6/2011 | Nagano | D04H 1/559 |
| | | | 607/114 |

FOREIGN PATENT DOCUMENTS

| EP | 1782774 A1 | 5/2007 |
| EP | 1994915 A1 | 11/2008 |

(Continued)

OTHER PUBLICATIONS

Hitoshi Usui, English Translation of Thermal body, 2016, Mycoal (Year: 2016).*

(Continued)

*Primary Examiner* — Tigist S Demie
(74) *Attorney, Agent, or Firm* — Osha Bergman Watanabe & Burton LLP

(57) ABSTRACT

A heating body, in which a heat-generating composition that generates heat in the presence of air, is accommodated in a bag body formed by heat sealing a one-surface side laminated base material including a first base material and a second base material, and a covering material, at a peripheral edge portion thereof. The first base material has a nonwoven fabric layer and a heat sealable resin layer; and the second base material is a sheet in which an olefin-based nonwoven fabric layer and a resin film are laminated using an olefin-based resin. The first base material and the second base material are capable of forming a space into which a body part can be inserted or held. The heat sealable resin layer and the nonwoven fabric layer are bonded together, (Continued)

and the resin film of the second base material and the covering material are bonded together.

5 Claims, 8 Drawing Sheets

(58) Field of Classification Search
CPC ........ A61F 2007/022; A61F 2007/0223; A61F 2007/0225; A61F 2007/0228; A61F 2007/038; A61F 7/032; A61F 7/034
See application file for complete search history.

(56) References Cited

FOREIGN PATENT DOCUMENTS

| JP | 2003-205556 A | 7/2003 |
|---|---|---|
| JP | 2005-328852 A | 12/2005 |
| JP | 3204312 U * | 5/2016 |

OTHER PUBLICATIONS

Extended European Search Report issued in European Application No. 18817599.6, issued Feb. 17, 2021 (9 pages).
International Search Report issued in International Application No. PCT/JP2018/022742, mailed Aug. 21, 2018 (1 page).
Written Opinion issued in International Application No. PCT/JP2018/022742, mailed Aug. 21, 2018 (4 pages).

* cited by examiner

HEATING BODY AND METHOD FOR PRODUCING THE SAME

TECHNICAL FIELD

The present invention relates to a heating body such as a chemical body warmer (warmer) that generates heat by reacting with air (oxygen) and a hot pack structure, and a method for producing the same.

BACKGROUND ART

Various products of heating bodies that use heat-generating compositions that generate heat upon contact with air have been developed, and generally widely used heating bodies are those of a type which is to be attached to clothing or a body, and another type which is not to be attached.

Conventional heating bodies such as a disposable warmer of a type (hand warmer type) that is not attached to clothing or the body are basically assumed to be used by being held by hand. In addition, the heating body having a member for being worn on a hand without being attached has been developed.

For example, Patent Document 1 discloses that a pocket for inserting a hand or the like is provided by bonding an insertion portion-forming material by heat sealing to the outside of a bag body (exothermic main body) encapsulating a heat-generating composition. However, in a case of such a heating body, there are disadvantages such as that it is necessary to perform heat-sealing processes with different temperature settings a plurality of times for one heating body. Patent Document 2 describes a heating body, in which a first base material having a separable line parallel to a longitudinal direction and a second base material not provided with the separable line are laminated, and a heat-generating composition is accommodated between the second base material and a covering material laminated on the second base material. It discloses that a sheet having a heat-sealing layer on the back surface of a nonwoven fabric is used as each of the first base material, the second base material, and the covering material, and that peripheral edge portions thereof are bonded together by a single heat-sealing simultaneously with the encapsulation of the heat-generating composition.

In a case of fixing other sheet onto the nonwoven fabric surface of the base material having a nonwoven fabric, usually, a sealable nonwoven fabric (nonwoven fabric with a melting point of about 110° C. to 123° C.) is generally used and the sheet is fixed by heat sealing or ultrasonic waves. However, in a case of using a producing machine and a producing method used in industrial production of a heating body such as a conventional disposable warmer, a method of bonding using ultrasonic waves is not suitable. In addition, even in a case of being bonded by heat sealing, sufficient strength is not obtained for using by inserting a hand, and there is a tendency to peel between the layers of the nonwoven fabric.

In particular, in a case of producing with a high-speed producing method that simultaneously performs bag making and encapsulation of heat-generating composition using a rotary heat-sealing roll, a seal (horizontal seal) in the direction (axial direction) orthogonal to the flow direction (MD) has a shorter heating contact time compared with a seal (vertical seal) parallel to the flow direction (longitudinal direction), and therefore, tends to have a weaker seal strength. On the other hand, the vertical seal tends to have a defect (so-called edge breakage) that a packaging material is cut at the edge of sealing due to higher surface pressure and orientation of resins of a film. Therefore, in such high-speed production, it is difficult to stack and bond another sheet on the nonwoven fabric surface, and it was not possible to realize a heating body having sufficient strength at a portion into which the hand is inserted.

CITATION LIST

Patent Documents

Patent Document 1: Japanese Provisional Patent Publication JP 2005-328852 A
Patent Document 2: Japanese Registered Utility Model No. 3204312

SUMMARY OF THE INVENTION

Problem to be Solved by the Invention

An object of the present invention is to eliminate the above-described inconveniences in the producing of the conventional heating body that can be worn on a body or the like without being attached, and to provide a heating body that is easy to produce, particularly enables high-speed production using a conventional rotary heat-sealing roll, has a wearing portion with sufficient strength for using by inserting a hand or the like, and thereby being used safely and conveniently, as well as a method for producing such a heating body easily and rapidly.

Means for Solving Problem

According to the present invention, there are provided:
[1] a heating body in which a heat-generating composition that generates heat in the presence of air is accommodated in a bag body formed by heat sealing a one-surface side laminated base material comprising a first base material and a second base material, and a covering material, at a peripheral edge portion thereof, characterized in that:
the first base material has one surface being a nonwoven fabric layer and the other surface being a heat sealable resin layer;
the second base material is a sheet in which an olefin-based nonwoven fabric layer and a resin film are laminated using an olefin-based resin;
the first base material and the second base material are capable of forming a space into which a body part can be inserted or held, in a part surrounded by the peripheral edge portion; and
in a heat sealed part of the bag body peripheral edge portion, the heat sealable resin layer of the first base material and the nonwoven fabric layer of the second base material are bonded together, and the resin film of the second base material and the covering material are bonded together;
[2] the heating body according to the above [1], wherein the resin constituting the olefin-based nonwoven fabric layer of the second base material has a melting point of 130° C. or higher and 160° C. or lower;
[3] the heating body according to the above [1] or [2], wherein both of a bonding strength between the first base material and the second base material and a bonding strength between the second base material and the covering material are 0.75 kgf/15 mm or more in four locations of the peripheral edge portion of the heating body;

[4] the heating body according to any one of the above [1] to [3], wherein the first base material is provided with at least one slit or a separable line;

[5] the heating body according to the above [4], wherein the separable line has a straight line or a wavy line perforation;

[6] a method for continuously producing a heating body in which a heat-generating composition that generates heat in the presence of air is accommodated in a bag body formed of a one-surface side laminated base material comprising a first base material and a second base material, and a covering material, by using a rotary roll type heating body-producing machine having a guide that transports the one-surface side laminated base material and the covering material, one or more sets of rotary heat-sealing rolls, and one set of cutting rolls, the method comprising steps of:

transporting each of the one-surface side laminated base material in which the first base material having one surface of a nonwoven fabric layer and the other surface of a heat-sealable resin layer and the second base material which is a sheet obtained by laminating an olefin-based nonwoven fabric layer and a resin film using an olefin-based resin are stacked, the covering material, and the heat-generating composition, to the rotary heat-sealing rolls having a recess that can be filled with the heat-generating composition and a sealing surface that heat-seals at the peripheral edge portion thereof, and heat-sealing the peripheral edge portion by the rotary heat-sealing roll so that the heat-sealable resin layer of the first base material and the nonwoven fabric layer of the second base material are bonded and the resin film of the second base material and the covering material are bonded while encapsulating the heat-generating composition between the second base material and the covering material;

[7] the producing method according to the above [6], wherein a temperature of the sealing surface during heat sealing is 130° C. or higher and 190° C. or lower;

[8] the producing method according to the above [6], wherein a temperature of the sealing surface during heat sealing is 145° C. or higher and 175° C. or lower;

[9] the producing method according to any one of the above [6] to [8], wherein the first base material and the second base material are temporarily fixed in advance so that a space in which a body part can be inserted or held in a part surrounded by the peripheral edge portion can be formed;

[10] the producing method according to any one of the above [6] to [9], wherein a rotational speed of the rotary heat-sealing roll is 5.0 m/min or higher; and

[11] the producing method according to any one of the above [6] to [10], wherein both of a bonding strength between the first base material and the second base material and a bonding strength between the second base material and the covering material are 0.75 kgf/15 mm or more in four locations of the peripheral edge portion of the heating body.

Effect of the Invention

According to the present invention, a heating body that has excellent bonding strengths of packaging materials, and is suitable for using by being worn on a body or the like by inserting a hand or the like without being attached, can be easily produced by a high-speed producing machine and a producing method using rotary heat-sealing rolls similar to the conventional one.

The heating body of the present invention has a first base material capable of forming a member that can be utilized as a pocket or a handle into which a hand or a finger etc. can be inserted. According to the present invention, the first base material bonded to the nonwoven fabric surface of the second base material has sufficient seal strength even in a case of high-speed production, and thus a problem such as peeling during use hardly occurs. In particular, both vertical seal and horizontal seal have similar optimum seal strengths, and the occurrence of defective products due to defective seals or edge breakages can be reduced or avoided. Therefore, according to the present invention, productivity and economy in the production are greatly improved.

The non-adhering type disposable warmer of the present invention in such a form can be used as-is, as a normal hand warmer that is held by a hand without being worn on the body or the like, and can be worn on the body by inserting a hand or the like into a slit of the first base material or a slit generated by cutting a separable line of the first base material. Thus, various usage methods can be freely selected.

In a case of using by inserting a hand, by wearing it with the heat-generating composition facing to the back side of the hand, the back of the hand can be warmed, which is said to be effective in restoring a function of the hand. In addition, in this type of usage, the back of the hand can be warmed while moving fingers, so that it can be used in various scenes for obtaining a desired thermal effect, such as typing smoothly when using a PC, improving the feeling of a terminal tackle when a fish hits during fishing, improving the feeling of pulling a trigger when hunting.

The heating body of the present invention will be mainly described with a case where it is worn on the hand, but the body part to be worn is not limited to the hand, and may be a finger, an arm, or the like, and for example, if a stretchable base material is used for the first base material, it can also be used as a supporter-type warmer that fits on the elbow or knee.

MODE(S) FOR CARRYING OUT THE INVENTION

Figure 1:
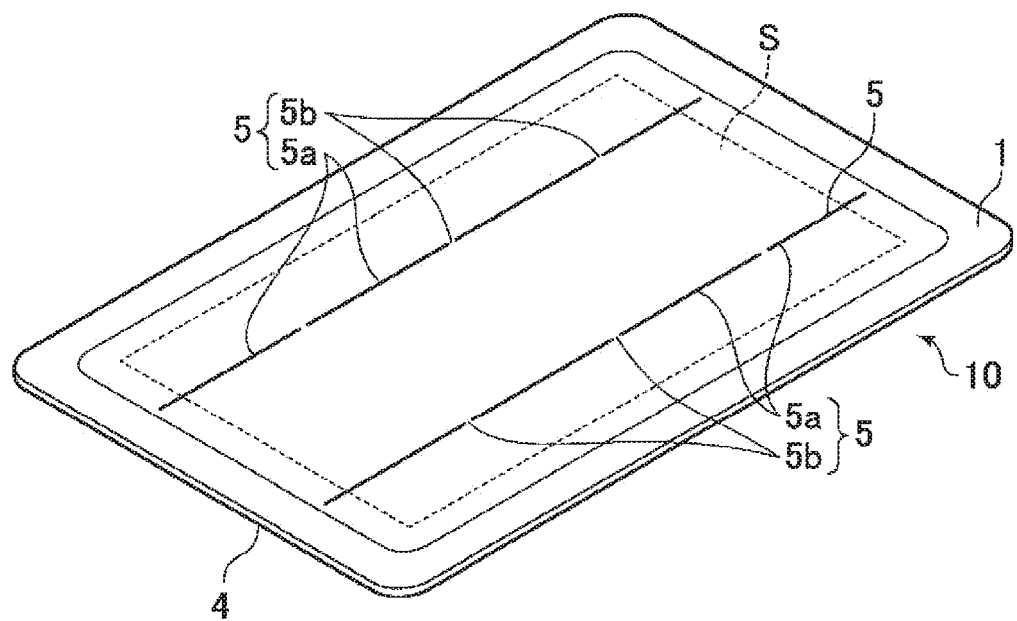
FIG. 1 is a perspective view of an embodiment of a heating body of the present invention.

A heating body of the present invention has a bag body accommodating a heat-generating composition, one side of which has a laminated structure of a first base material and a second base material. Both of these base materials are configured such that they are not firmly attached together all over, but are bonded at a peripheral edge portion and comprise in other part a non-bonded part (including a state of easily separable by hand). A space in which a body part such as a hand can be inserted or held is formed in this non-bonded part.

The first base material and the second base material form a bag body by being heat-sealed with a packaging material (covering material) constituting the other side of the bag body. In the producing method of the heating body using high-speed rotary heat-sealing rolls, the heat-generating composition is encapsulated between the second base material and the covering material during the laminated first base material and the second base material, and the covering material are bonded by a single heat-sealing to form a bag body.

In a bag body for accommodating a heat-generating composition, at least one of the second base material and the covering material is composed of an air-permeable packaging material in order to cause the heat-generating composition to generate heat. In order to obtain a sufficient thermal feeling when inserting a hand or the like, the covering material preferably has air-permeability. The first base material is optionally set to be air-permeable, but in order to have heat insulation properties, it is preferably non-air-permeable or low air-permeable.

The air-permeable packaging material that can be used for the bag body in the present invention may be a film or sheet that is completely or partially air-permeable, and as long as the requirements of the first base material, the second base material, or the covering material described below are satisfied, can be a single-layered or laminated, porous film or a sheet can be used alone or in combination with a nonwoven fabric or the like, or a single-layered or laminated, non-porous film or a sheet with a needle hole(s), either alone (including a single layer and laminated layers; the same shall apply hereinafter) or in combination with a nonwoven fabric or the like. In the present invention, "film" mainly refers to one that is alone or relatively thin, and "sheet" mainly refers to one that is alone or a laminate of two or more layers, or relatively thick, but those terms are not strictly distinguished.

In the present invention, as the air-permeable film or sheet, a stretched film, preferably a stretched porous film or a sheet comprising the film, or a needle-hole processed non-air-permeable film or sheet is suitably used.

The air-permeability of the packaging material that constitutes the bag body for accommodating a heat-generating composition can be appropriately selected and used so that the heat generation characteristics (rise rate of heat generation, duration of heat generation, heat transfer to the object to be heated, such as a human body and clothing) are in a desired range depending on the purpose of use, because the heat generation characteristics of the heating body change depending on the selection of air-permeability.

For general body warmers and the like, air-permeable packaging materials of 10,000 to 40,000 seconds/100 cc (JIS P8117) are used in a case of a porous film or the like. In addition, for example, for a warmer for use in shoes, those with 2,000 to 7,000 seconds/100 cc are used. Therefore, as an air-permeable packaging material of a bag for accommodating a heat-generating composition, a packaging material having air-permeability of 2,000 to 40,000 seconds/100 cc is generally used. In a case of a film or the like that has air-permeability conferred by needle hole processing, a packaging material of 2 to 6 seconds/100 cc is generally used. In a case of a heating body designed to be used at a high temperature and/or in a short time, such as a meridian stimulation warming tool, a packaging material of 0 to 10,000 seconds/100 cc can be used.

First Base Material

In the heating body of the present invention, as the first base material, a sheet of two or more layers in which one of the surfaces is a nonwoven fabric layer and the other is a heat-sealable resin layer is used. The first base material may have one or more other layers (for example, a layer or layers of other resin having no heat-sealability) between the nonwoven fabric layer and the heat-sealable resin layer, depending on the purpose. Moreover, the nonwoven fabric layer and the heat-sealable resin layer may each be a multilayer.

In the first base material, the nonwoven fabric layer and the heat-sealable resin layer (and optionally other layers) can be laminated by any method. In addition, the first base material may or may not be stretchable.

The nonwoven fabric of the first base material is not particularly limited, and may be any kind of nonwoven fabric. For example, those conventionally used in the technical field such as a heating element and a medical heating tool can be suitably used. Specifically, the nonwoven fabrics include those comprising artificial fibers such as nylon, vinylon, polyester, rayon, acetate, acrylic, polyethylene (PE), polypropylene (PP), polyvinyl chloride, and polyethylene terephthalate (PET), and natural fibers such as cotton, hemp, and silk; and include nonwoven fabrics in the form or producing method such as spunbond, thermal bond, and spunlace. The basis weight of the nonwoven fabric changes depending on specific gravity of the nonwoven fabric material and bulkiness due to a difference in an entanglement method, and general, it is suitably about 10 g/m$^2$ to about 200 g/m$^2$, with about 10 g/m$^2$ to about 100 g/m$^2$ particularly preferable.

The heat-sealable resin layer of the first base material is not particularly limited and any kind thereof may be used as long as it has heat-sealability. As the heat-sealable resin layer of the first base material in the present invention, an olefin-based resin is particularly preferable, among which polyethylene is preferable, particularly low density polyethylene (LDPE), linear low density polyethylene (LLDPE), and metallocene-catalyzed linear low density polyethylene (mLLDPE) are most preferable.

As a resin of an additional layer that may be present, a thermoplastic synthetic resin or the like is generally used. Specifically, polyethylene, polypropylene, polyester, polyamide, polyvinyl alcohol, polyvinyl chloride, polyvinylidene chloride, polyurethane, polystyrene, ethylene vinyl acetate copolymer (EVA), polycarbonate, and the like are suitably used alone or in combination.

A thinner first base material is better in terms of heat transfer, and the production can be carried out economically without extremely raising the temperature or reducing the speed of a warmer-producing machine. Accordingly, it is most preferable that the nonwoven fabric of the first base material has a basis weight of 15 to 40 $g/m^2$ and the resin film layer has a thickness of 15 to 40 μm.

In the first base material, slit(s) or separable line(s) in various forms, sizes, positions, directions, and number as described later can be formed by a known method as desired in order to allow insertion of a body part such as a hand into a space formed between the first base material and the second base material.

As a member used in a case where the first base material needs stretchability, any member as long as it has stretchability may be used, and a fabric, a woven fabric, a nonwoven fabric, a film, a sheet, an aggregate of a plurality of strips, and the like may be used. Particularly, a stretchable film, a stretchable sheet, a stretchable flat plate, a stretchable net, a stretchable nonwoven fabric, and the like are exemplified. Since those formed of natural rubber, synthetic rubber, or thermoplastic elastomers are highly stretchable and easy to handle, and moreover, since the thermoplastic elastomer has heat-fusibility, they make producing a laminate very easy, and are desirable. A mixture containing the natural rubber, synthetic rubber, or thermoplastic elastomer can also be used. In addition, a thermoplastic stretchable base material which consists of polyolefins such as polyethylene, polypropylene, polybutene, and an ethylene vinyl acetate copolymer, a mixture of a butadiene resin such as 1,2-polybutadiene and an aromatic vinyl compound-conjugated diene block polymer, thermoplastic rubbers, thermoplastic elastomers, and a mixture of these with polyolefins can be used as a material having an excellent economic efficiency and stretchability.

In a case where a member that does not require stretchability is used for the first base material, any material that is substantially non-stretchable may be used, and examples thereof include polymeric materials such as polyethylene, polypropylene, polyester, polyvinyl chloride, polyvinylidene chloride, polyurethane, polystyrene, a saponified ethylene vinyl acetate copolymer or an ethylene vinyl acetate copolymer, polycarbonate, aromatic or aliphatic polyamide, polysulfone, polyvinyl alcohol, polyacrylonitrile, a vinyl chloride-vinylidene chloride-based resin, polyimide, hydrochloric acid rubber, polyphenylene, polyphenylene oxide, polyphenylene sulfide, polyamideimide, an epoxy resin, polyaminobismaleimide, polyacetal, polyetheretherketone, polyethersulfone, polyarylate, and polyoxybenzyl, paper, pulp, textile by natural materials such as fibers or combinations thereof, woven fabrics, nonwoven fabrics, films, sheets, and foamed sheets. In addition, the examples also include substantially non-stretchable substances such as a stretchable base material that has been provided with a pressure-sensitive adhesive or adhesive made of the polymer material or the polymer material and/or the monomer thereof, or that has been biaxially stretched.

In addition, two or more kinds thereof can be laminated and used.

Second Base Material

In the heating body of the present invention, as the second base material, a sheet in which an olefin-based nonwoven fabric layer and a resin film are laminated with an olefin-based resin is used. The second base material may or may not be stretchable, but is preferably non-stretchable.

One surface of the second base material, which is the surface on the first base material side, is covered with a olefin-based nonwoven fabric. Nonwoven fabrics are difficult to conduct heat and have low thermal conductivity, so that low temperature burns can be prevented. In addition, the nonwoven fabrics have a soft touch and can improve the touch as compared with the resin film.

Here, examples of the olefin-based resin include a polyethylene-based resin, a polypropylene-based resin, and an ethylene vinyl acetate copolymer. Examples of the polyethylene-based resin include high density polyethylene, low density polyethylene, and linear low density polyethylene. Examples of the polypropylene-based resin include homopolypropylene and random polypropylene.

The olefin-based nonwoven fabric of the second base material is preferably one comprising at least the above-mentioned olefin-based resin, particularly a polyethylene-based resin or a polypropylene-based resin. The fiber constituting the nonwoven fabric may be a composite fiber containing a plurality of resins, a mixed fiber, or the like, and the melting point of the fiber constituting the nonwoven fabric is preferably 130° C. or higher, and more preferably 135° C. or higher. The upper limit of the melting point may be about 160° C., preferably 150° C. or lower, and more preferably 140° C. or lower. In a case of the composite fiber having a core-sheath structure, the melting point of the fiber constituting the surface (sheath) is preferably in the above range. Examples thereof include a composite fiber in which the core is polyester and the sheath is high density polyethylene and a composite fiber in which the core is polypropylene and the sheath is high density polyethylene. The nonwoven fabrics in the form or producing method such as spunbond, thermal bond, or spunlace are included. The basis weight of the nonwoven fabric changes depending on specific gravity of the nonwoven fabric material and bulkiness due to a difference in an entanglement method, and generally, about 10 $g/m^2$ to about 200 $g/m^2$ is suitable, with about 10 $g/m^2$ to about 50 $g/m^2$ most preferable. A nonwoven fabric having a low density and a good texture is particularly desirable, for example an oven type of a thermal bond method (nonwoven fabric bonded with hot air passing through a web in an oven where hot air is generated at a high temperature).

As the resin film of the second base material, a single-layer or multi-layer sheet of polyethylene, polypropylene, polyester, polyamide, polyvinyl alcohol, polyvinyl chloride, polyvinylidene chloride, polyurethane, polystyrene, ethylene vinyl acetate copolymer, polycarbonate, and the like are used. As the resin film of the second base material in the present invention, an olefin-based resin is particularly preferable, and polyethylene is more preferable. Particularly, low density polyethylene (LDPE), linear low density polyethylene (LLDPE), and metallocene-catalyzed linear low density polyethylene (mLLDPE) are most preferable. As a thickness of the resin film of the second base material, generally, about 10 μm to 100 μm is suitable, and particularly, about 30 μm to 60 μm is most preferable.

The nonwoven fabric and the resin film of the second base material are formed into a laminated sheet in advance by lamination with a resin. The laminating method may be any of an extrusion laminating method, a curtain spray method, a dry laminating method, and the like, and an extrusion laminating method is preferable. The resin used in the laminate of the second base material is preferably an olefin-based resin, and examples of the olefin-based resin include a polyethylene-based resin, a polypropylene-based resin, and an ethylene vinyl acetate copolymer. Examples of the polyethylene-based resin include high density polyethylene, low density polyethylene, and linear low density polyethylene. Examples of the polypropylene-based resin include homopolypropylene and random polypropylene. The melting point of the resin used in the laminate of the second base material is preferably 90° C. or higher, and is more preferably 100° C. or higher. The upper limit of the melting point is preferably 130° C. or lower, and is more preferably 120° C. or lower. As the thickness of the laminate layer, generally, about 5 μm to 100 μm is suitable, and particularly, about 10 μm to 50 μm is most preferable. In the present invention, the resin of the laminate layer plays an important role with respect to the bonding strengths between the first base material and the second base material and between the second base material and the covering material. In addition, the heat sealability with the first base material improves as the laminate resin penetrates the nonwoven fabric layer, and thus it is also preferable to actively introduce the laminate resin during lamination by using a nip roll such as chlorosulfonated polyethylene rubber (for example, trade name "Hypalon") with high hardness.

Most preferably, the second base material has a thickness of 70 μm or less, or the basis weight of the nonwoven fabric layer of the second base material is 25 g/m$^2$ or less.

By using the sheet as described above as the second base material, the first base material and the second base material as well as the second base material and the covering material are firmly bonded, even by heat-sealing in a short time at a relatively low temperature by high-speed producing.
Covering Material The covering material used for the heating body of the present invention is not particularly limited as long as it can be bonded to the second base material by heat sealing. For example, it may be a single layer or a laminate of a resin film having air-permeability such as a porous film, or may be a laminate of a nonwoven fabric and a porous film. Further, a film or the like having no or low air-permeability can be used as a covering material by providing with a hole by a needle or laser or the like. For example, a laminated sheet in which a polyethylene terephthalate spunlace nonwoven fabric and a polyethylene-based film are laminated by extrusion of a LDPE resin can be used.

In a case of laminating, any conventionally known method can be applied. For example, it may be any of various laminating methods or a method of laminating by heat bonding or using adhesives such as hot melt adhesive or an acrylic-based or urethane-based adhesive, and the bonding may be performed on the entire surface or may be partially performed on the surface to maintain flexibility. Preferably, an extrusion lamination method, a curtain spray method, or a dry lamination method is used.

The film resin layer of the covering material is not particularly limited, and any kind thereof may be used as long as it has heat-sealability. As the film resin layer of the covering material in the present invention, an olefin-based resin is particularly preferable; polyethylene, particularly low density polyethylene (LDPE), linear low density polyethylene (LLDPE), and metallocene-catalyzed linear low density polyethylene (mLLDPE), are most preferable.

As a resin of an additional layer that may be present, a thermoplastic synthetic resin or the like is generally used. Specifically, polyethylene, polypropylene, polyester, polyamide, polyvinyl alcohol, polyvinyl chloride, polyvinylidene chloride, polyurethane, polystyrene, ethylene vinyl acetate copolymer, polycarbonate, and the like are suitably used alone or in combination.

As the thickness of the film resin layer of the covering material, generally, about 10 μm to 100 μm is suitable, and about 20 μm to 80 μm is most preferable.

As a fiber of the nonwoven fabric that can be used for the covering material, polypropylene-based fibers and polyester-based fibers such as polyethylene terephthalate, polypropylene terephthalate, and polybutylene terephthalate are suitable from the viewpoint of heat resistance, hydrophobicity, strength, or flexibility. They are also preferable from the viewpoint of heat retention during use of the heating body, because those are difficult to transmit heat and have low thermal conductivity. As the basis weight of the covering material nonwoven fabric, generally, about 10 g/m$^2$ to 200 g/m$^2$ is suitable, and about 10 g/m$^2$ to 100 g/m$^2$ is most preferable.

If necessary, as disclosed in JP 2009-197385 A, a nonwoven fabric with a constant heat retention efficiency of 60% or more in the atmosphere of a temperature of 20° C. and a humidity of 65% conferred by increasing the thickness of the nonwoven fabric even with the same basis weight and reducing a contact area of a nonwoven fabric surface layer fiber may be used. In this way, it is possible to use, as a nonwoven fabric structure, those having heat retention effects such as both of a heat retention effect of an air layer with bulkiness of the nonwoven fabric and a heat retention effect derived from the thermal conductivity of the material itself.

Further, as disclosed in JP 2011-218011 A, in a case where a heat-generating composition or a heat-generating portion is covered by forming a metal film on at least one surface of the nonwoven fabric of the covering material, the heat retention can be improved and, at the same time, high heat retention can be maintained for a long time. In the present invention, the "heat-generating portion" refers to a portion in which the heat-generating composition is accommodated by the second base material and the covering material.
Heat-Generating Composition The heat-generating composition in the heating body of the present invention is not limited in the type and any conventionally known member that generates heat in the presence of air can be applied. Among them, a heat-generating composition using metallic powder is suitably used. The heat-generating composition used in the present invention usually contains at least metallic powder, salts, water, and a water retention agent (activated carbon).

As a metallic powder, iron powder is generally used, but any metallic powder other than iron powder may be used as long as it generates oxidation heat. As a salt, inorganic salts such as sodium chloride, potassium chloride and magnesium chloride are generally used. As a water retention agent, activated carbon is generally used, and a water retention agent other than the activated carbon (for example, a water absorptive polymer, vermiculite, sawdust, a silica-based material) may be contained. Further, as necessary, conventionally known various other components can be added.

As a specific composition example of the heat-generating composition, it is suitable to use a composition formulated with a proper formulation of heat-generating raw materials such as iron powder, reduced iron, activated carbon, alumina, silica gel, charcoal, water absorptive polymer, sodium chloride, potassium chloride, calcium chloride, magnesium chloride, iron chloride, acetic acid, chloroacetic acid, water, an acrylic-based water absorptive polymer, CMC, bentonite, tourmaline (mafic tourmaline), sodium tripolyphosphate, slaked lime, vermiculite, wood flour, polyethylene, polypropylene, and polystyrene.

Formulation examples of blending these components include, for example, a heat-generating composition containing 35 to 80% by weight of iron, 1 to 20% by weight of activated carbon, 1 to 10% by weight of salt, 5 to 45% by weight of water, and 0 to 45% by weight of the water retention agent other than the activated carbon, based on the weight of the heat-generating composition regarded as 100%.

The heat-generating composition can be produced by mixing indispensable components and optional components selected as necessary as described above under low oxygen or anoxic condition by a known method. The heat-generating composition may be in any form as long as it is to be a state accommodated in an air-permeable bag body, and may be a powder, which may be further processed by a known method. For example, it may be formed into shapes such as a sheet shape by rolling, a cube shape by tableting, or the like. Further, it may be used in a desired form such as clay, viscous body, ink, cream, slurry or liquid.

Production Method

The heating body of the present invention can be produced by setting on a table a covering material with the nonwoven fabric surface facing down and the heat sealing layer facing up, on top of that, placing a heat-generating composition formed smaller than the covering material, further stacking thereon a second base material with the resin film layer facing down so as to cover the heat-generating composition and further thereon a first base material with the heat-sealable resin layer facing down, and heat-sealing the peripheral edge portion at a predetermined temperature by a heat-sealing device.

Furthermore, by using a rotary heat-seal roll type producing machine normally used in the industry, wherein a series of bag making and encapsulation of the heat-generating composition by heat-sealing as described above is performed on the rotary roll, the heating body of the present invention can be produced continuously from a long packaging material.

The rotary roll type producing machine for a heating body is made such that a plurality of rectangular or other shape of heating bodies are continuously obtained, by continuously supplying and heat-sealing a long packaging material and a heat-generating composition so as to form heating bodies in a shape such as a rectangular shape to be adjacent in the longitudinal direction, and cutting the adjacent portion of the adjacent heating bodies. In a case of producing the heating body of the present invention, this rotary roll type producing machine is configured to include a guide(s) for transporting a sheet-like base material (one-surface side laminated base material) in which the first base material and the second base material are stacked and for transporting the covering material, one or more sets of rotary heat-sealing rolls and one set of cutting rolls. The rotary heat-sealing roll is provided with a substantially box-shaped recess with which the heat-generating composition can be filled, and the periphery of the recess has a sealing surface having, for example, a width of 14 mm in the longitudinal direction and a width of 18 mm in the axial direction. Further, a cross-sectional shape of the sealing surface is formed in an uneven shape, and a curve (R) having a curvature radius of 1 mm, for example, can be provided at the end of the sealing surface. The rotary roll type producing machine may further include a heat generating composition supply means (hopper) for supplying the heat generating composition to the recess of the heat-sealing roll.

The sheet-like base material obtained by stacking the first base material and the second base material, and the covering material, as the packaging materials of the heating body are stacked in advance or during transportation, and they are sealed, first at the front end side by rotary heat-sealing rolls in an axial direction of the rolls, then along the longitudinal direction while the heat-generating composition is supplied from the heat-generating composition supply means, and further at the rear end side in the axial direction of the rotary heat-sealing rolls, so that a heat-generating composition is encapsulated. In this connection, the rotary heat sealing is performed using a low melting point film as a heat sealing layer, in such a manner that by the rotary heat-sealing rolls the stacked sheet-like base material and the covering material are heated from both surfaces to cause melting of the low melting point film located inside, pressed, and bonded. In the rotary heat-sealing rolls, appropriate temperatures and clearances can be set, and a curve (R) can be provided at the end of the sealing surface of the rotary heat-sealing rolls. With this, it is possible to produce continuously heating bodies having an excellent appearance of the sealed portion without causing edge breakage or wrinkle to occur in the sealed portion of the heating body.

According to the present invention, the temperature setting of the heat sealing rolls can be made equivalent to the conventional temperature condition, despite the addition of the first base material compared to a heating body such as a disposable warmer using a normal bag body, and the same strengths can be obtained for all of the seal in the axial direction on the front end side, the seals in the longitudinal direction, and the seal in the axial direction on the rear end side. For example, the covering material side can be set at a temperature in a range of 130° C. to 190° C., and the first base material side can be set at a temperature in a range of 130° C. to 190° C. Preferably, it is desirable to set the covering material side at a temperature in a range of 145 to 175° C., and the first base material side at a temperature in a range of 145 to 175° C. Furthermore, the heating body of the present invention can be continuously produced at a high speed by operating the rotary roll type producing machine as described above at a high speed.

Note that, "high speed" in the rotary roll type production refers to a speed of 5 m/min or more. In a general warmer producing machine, the production is performed at 5 m/min to 7 m/min.

In producing, the first base material and the second base material may be supplied to the producing machine from separate feeding shafts, but it is advantageous to preliminarily stack and temporarily fix them. By laminating and integrating them in this way, it is possible to use feed axes of the number equipped in a conventional warmer producing machine when producing a heating body. In addition, when used, the first base material and the second base material are easily peeled except at the heat-sealed peripheral edge portion, so that a hand or the like can be inserted smoothly from a slit, or a slit obtained by cutting a separable line, provided on the first base material.

In order to use by inserting the hand or the like under the first base material, it is considered necessary that at least the bond between the first base material and the second base material has a seal strength of about 0.6 kgf/15 mm or more.

In the heating body of the present invention, the bonding strength between the first base material and the second base material, and the bonding strength between the first and the second base materials and the covering material are preferably 0.65 kgf/15 mm or more, more preferably 0.75 kgf/15 mm or more, and most preferably 0.85 kgf/15 mm or more, in all of the four locations of the peripheral edge portion of the heating body. Here, the four locations of the peripheral edge portion of the heating body are four equally spaced points on the outer periphery of the heating body, and in the case of a quadrilateral heating body, it is preferable that there is one location on each side. Therefore, for example, for a rectangular heating body, each of the seals at the peripheral edge portion constituting the four sides, that is, the seals (horizontal seals on the front end side and the rear end side) in the direction (axial direction) orthogonal to the flow direction (MD) and the seals (vertical seals on both sides) parallel to the flow direction (longitudinal direction) preferably has a seal strength in the above range.

Measurement of the bonding strength can be performed as follows. A sample with a size of 15 mm width (for example, 15±0.5 mm×35±5 mm) is set in a tensile tester (for example, produced by Aikoh Engineering Co., Ltd., MODEL1301-D, 0113), and the tensile speed is set to 300 (mm/min) to start the measurement. When the sample is broken or the tensile movement stops, a measured MAX value is read. With this method, each of the bonding strengths between the first base material and the second base material and between the second base material and the covering material can be measured.

In addition, it is also possible to provide a drug layer containing an aromatic compound, a plant extract, a herbal medicine, fragrance, a slimming agent, analgesic, a blood circulation promoter, a swelling ameliorative agent, an antibacterial agent, a bactericidal agent, fungicide, deodorant, deodorant, a transdermally absorbable drug, a lipolytic component, a negative ion generator, a far-infrared radiator, a magnetic substance, a poultice, cosmetics, bamboo vinegar, wood vinegar or the like, in the heating body of the present invention.

Examples of the method of including a drug include applying the drug by spraying, and laminating a sheet or the like of absorbent cotton or nonwoven fabric in which a drug is contained on the heating body. Moreover, these drugs may be contained in one or both of two base materials.

Further, at least one of the first base material, the second base material, the heat-generating composition, and the covering material can contain a warming sensation agent and/or a cooling sensation agent. With this, the blood circulation promoting action can be further enhanced when using the heating body.

Any material generally used for pharmaceuticals or cosmetics including a warm feeling patch and a cold feeling patch can be used, such as pepper tincture, nonylic acid vanillylamide, and capsaicin, as the warming sensation agent, and menthol such as 1-menthol and dl-menthol and menthol derivatives (for example, menthyl lactate) as the cooling sensation agent.

Outer Bag

The heating body is tightly sealed in an outer bag that blocks oxygen, and stored until use. Such outer bags are also known.

How to Use

Specific embodiments and usage states of the heating body according to the present invention will be described with reference to the accompanying drawings.

Figure 2:
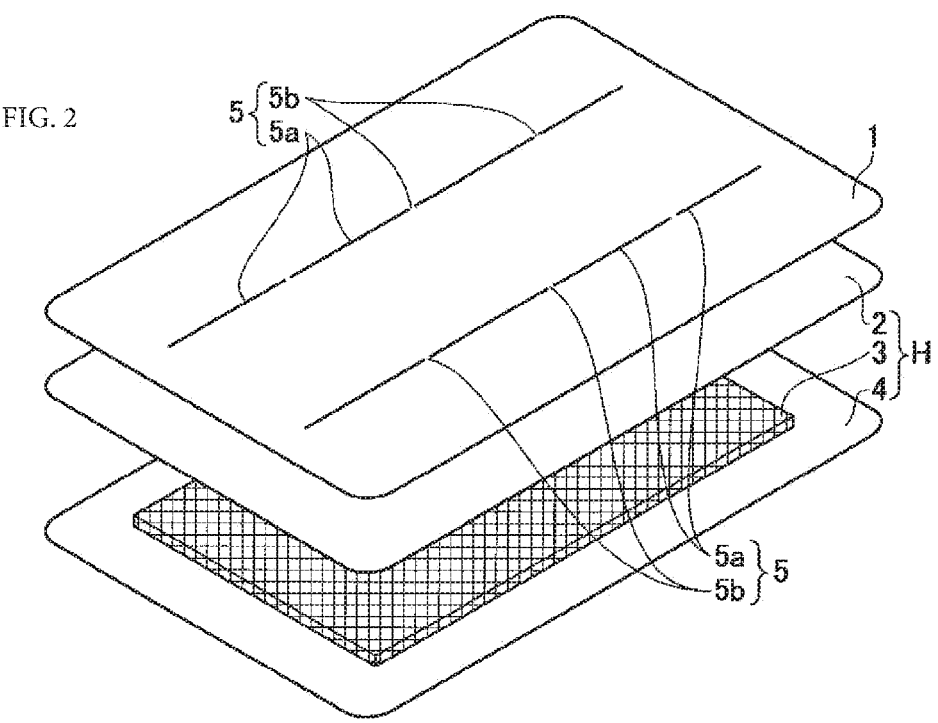
FIG. 2 is an exploded perspective view of the embodiment as illustrated in FIG. 1.

FIG. 1 is a perspective view illustrating an embodiment of the heating body of the present invention, and FIG. 2 is an exploded view for explaining each configuration.

Figure 3:
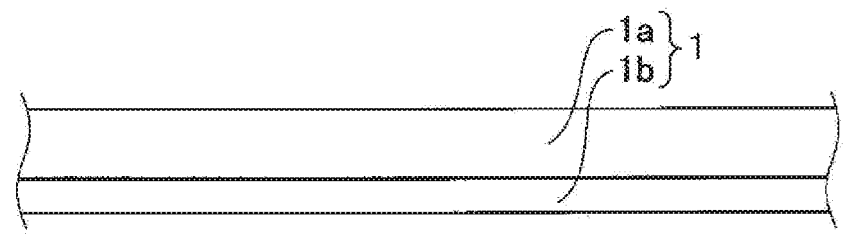
FIG. 3 is an enlarged end view of a first base material of the embodiment as illustrated in FIG. 1.
Figure 4:
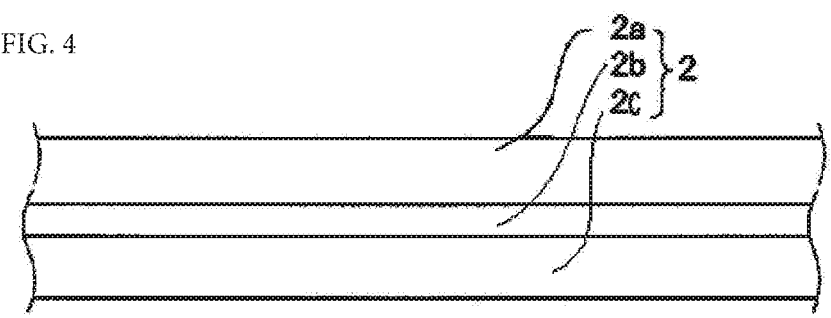
FIG. 4 is an enlarged end view of a second base material of the embodiment as illustrated in FIG. 1.
Figure 5:
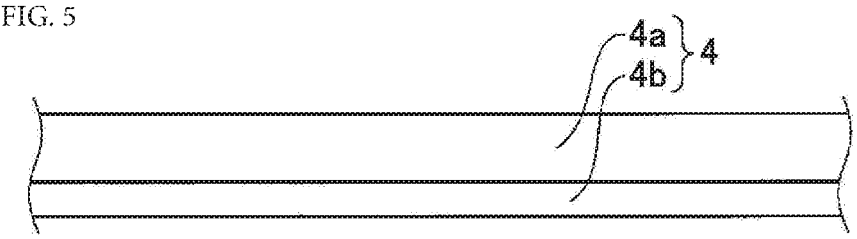
FIG. 5 is an enlarged end view of a covering material of the embodiment as illustrated in FIG. 1.

In the drawings, reference numeral 10 denotes a heating body, in which a first base material 1, a second base material 2, a heat-generating composition 3, and a covering material 4 are laminated in order from the top. As illustrated in FIG. 3, the first base material 1 is provided with a heat-sealable resin layer 1b on the back surface of a nonwoven fabric 1a; as illustrated in FIG. 4, the second base material 2 is provided with an extruded laminate layer 2b and a resin film (heat sealing) layer 2c on the back surface of a nonwoven fabric 2a; and as illustrated in FIG. 5, the covering material 4 is also provided with a heat sealing layer 4b on the back surface of a nonwoven fabric 4a.

Although the heating body 10 of the present embodiment is configured in a rectangular shape, it may have any shape such as a circle, an ellipse, or a gourd.

The first base material 1 and the second base material 2 are heat-sealed at their outer peripheral edges by the heat-sealable resin layer 1b provided on the back surface of the first base material 1, and a sealed insertion space S is formed between the first base material 1 and the second base material 2. In addition, the first base material 1 is provided with separable lines 5 and 5 formed of two parallel straight perforations along the longitudinal direction.

The second base material 2 and the covering material 4 are heat-sealed along the outer peripheral edge by the heat-sealing layer 2c and the heat-sealing layer 4b, and the heat-generating composition 3 is accommodated therebetween.

In the above embodiment, the first base material 1, the second base material 2, and the covering material 4 are bonded together in a laminated state by using the sealing layers 1b, 2c, and 4b provided on the back surfaces of the nonwoven fabrics 1a, 2a, and 4a, respectively. In addition to that, an adhesive layer or a fusion layer may be used supplementarily.

In addition, the first base material 1 may be a laminated plurality of nonwoven fabric 1a, and the layer located on the second base material 2 side may be a molten nonwoven fabric containing or blended with a low melting point material at least partially. For the second base material 2, too, the nonwoven fabric 2a may be a molten nonwoven fabric containing or blended with a low melting point material at least partially.

Next, usage examples of embodiment of the above heating body will be described.

Figure 6:
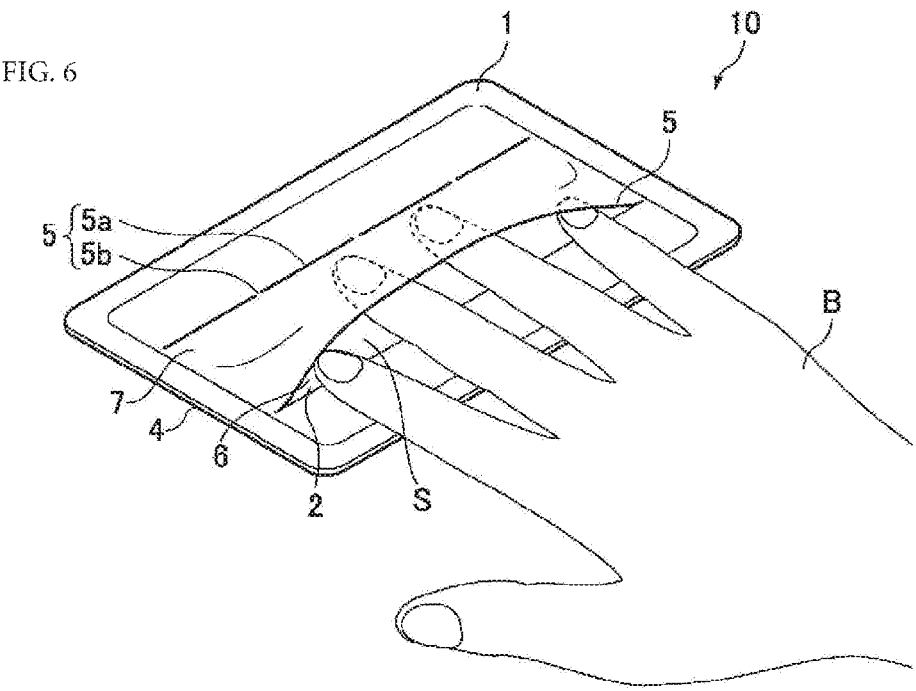
FIG. 6 is an explanatory diagram illustrating an example of use of the embodiment as illustrated in FIG. 1.

For example, as illustrated in FIG. 6, by cutting one separable line 5 of the first base material 1, an opening 6 is formed along the cut separable line 5, and from the opening 6, a part B of the body periphery such as a toe tip, an ear periphery, or a fingertip as illustrated in drawings can be inserted to a pocket-like insertion space S formed between the first base material 1 and the second base material 2.

Figure 7:
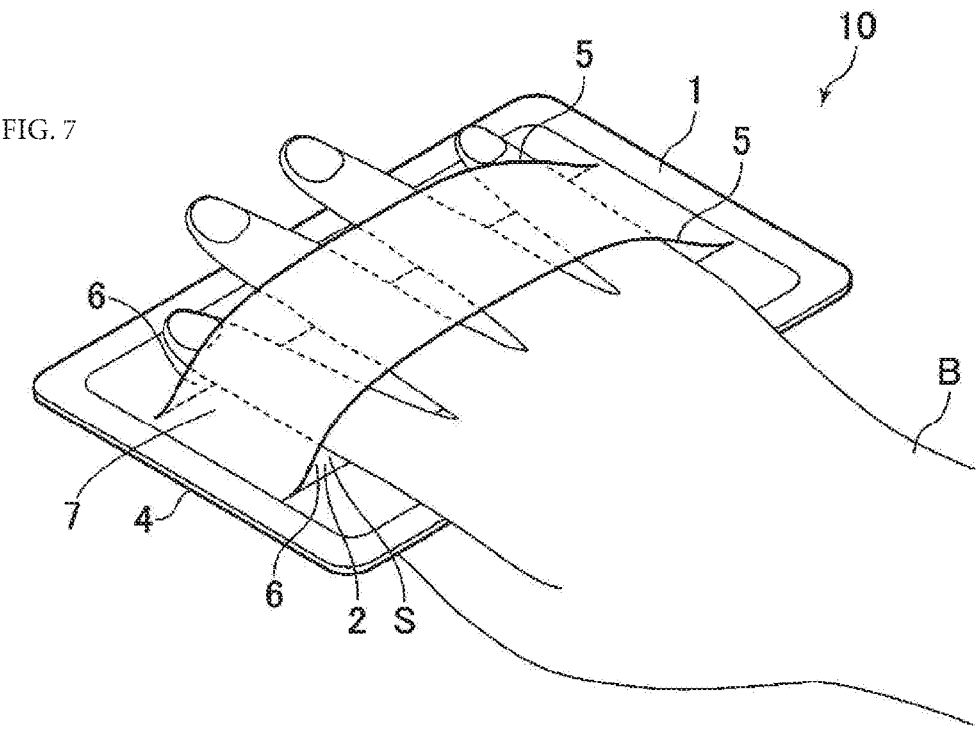
FIG. 7 is an explanatory diagram illustrating another example of use of the embodiment as illustrated in FIG. 1.
Figure 8:
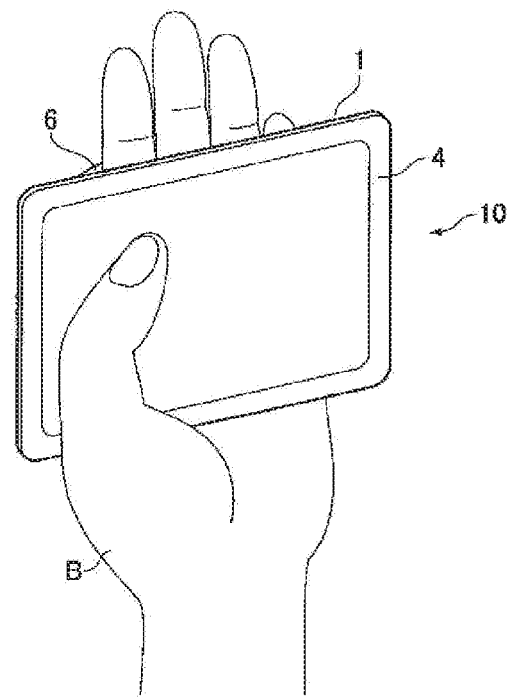
FIG. 8 is an explanatory diagram illustrating another example of use of the embodiment as illustrated in FIG. 1.

Also, as illustrated in FIGS. 7 and 8, when the two separable lines 5, 5 are cut, the fingertip B can be inserted into an insertion space S through one opening 6 of openings 6, 6, which are formed on the sides at both separable lines 5, 5 of a belt-like portion 7 formed in a portion sandwiched between these two cut separable lines 5, 5, and at least the end of the finger tip can be protruded from the other opening 6, so that the heating body 10 can be fixed to the fingertip B using the belt-like portion 7, and so that the fingertip B can be warmed in that state. In this way, when the heating body 10 is used by inserting the fingertip B into the insertion space S, it becomes possible to effectively warm a part of the body that is desired to be warmed, by simply wearing the heating body 10 on the part without gripping the heating body 10.

In addition, in FIGS. 7 and 8, the hand is inserted so that the palm is on the side of the heat-generating composition 3, but if the hand is inserted so that the back of the hand is on the side of the heat-generating composition 3, the inserted hand can be used freely. For example, it is possible to perform activities such as operating a mobile phone or a tablet or the like while wearing the heating body 10.

If it is used without cutting the separable line 5, it can be used in the same manner as a conventionally used heating body (a non-stick type disposable warmer).

As in the above embodiment, where the first base material 1, the second base material 2, and the covering material 4 are formed to have the heat sealing layers 1b, 2c, and 4b on the back surfaces of the nonwoven fabrics 1a, 2a, and 4a, respectively, in the heating body 10 of the present invention the heat sealing layers 1b, 2c, and 4b respectively provided on the first base material 1, the second base material 2, and the covering material 4 can be used for easy lamination. In particular, as in the present embodiment, where the outer shapes of the first base material 1, the second base material 2, and the covering material 4 are formed in the same rectangular shape, by preparing long sheet materials of the first base material 1, the second base material 2, and the covering material 4, continuous production can be performed very easily.

Figure 9:
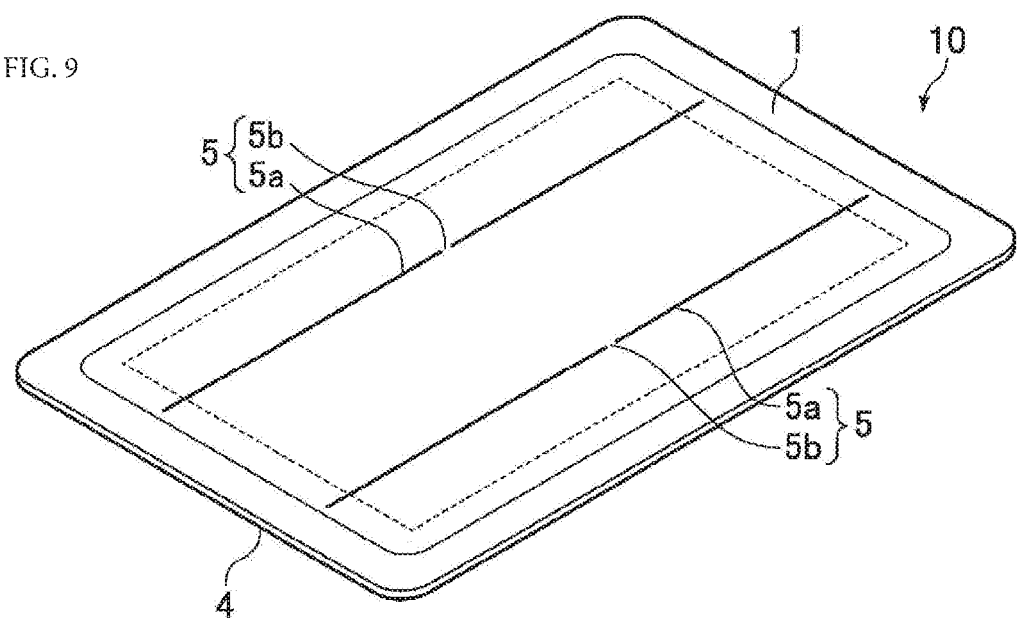
FIG. 9 is a perspective view of another embodiment of a heating body of the present invention.

Note that, the separable line 5 is formed in a linear perforation in which cut portions 5a and non-cut portions 5b are contiguous, but this perforation may have only one non-cut portion 5b as illustrated in FIG. 9. Alternatively, it may be a slit without the non-cut portion 5b.

Figure 10:
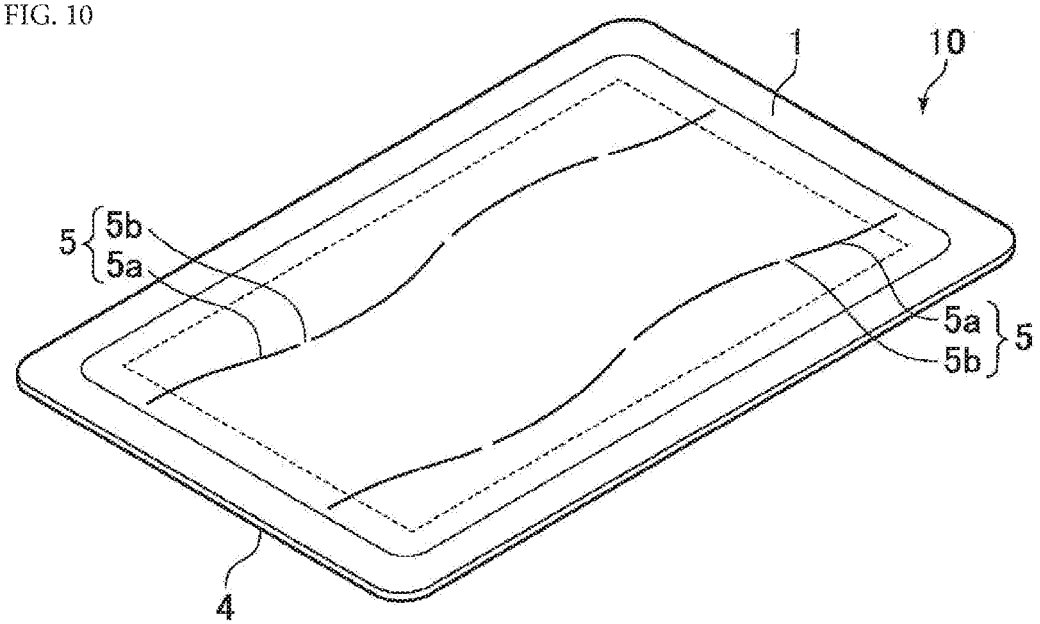
FIG. 10 is a perspective view of still another embodiment of a heating body of the present invention.

In addition, the separable line may be formed in a wavy perforation instead of a linear perforation as illustrated in FIG. 10, and the linear perforation and the wavy perforation may be used in combination.

Figure 11:
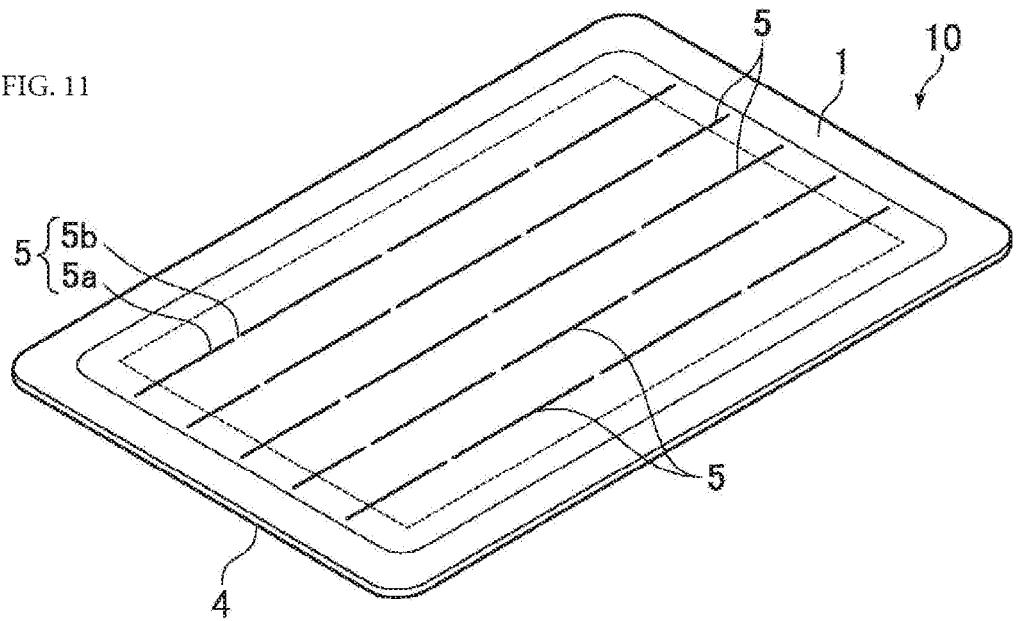
FIG. 11 is a perspective view of still another embodiment of a heating body of the present invention.

Further, the number of the separable lines 5 is not limited to two, and may be formed many, such as five as illustrated in FIG. 11. When providing a large number of the separable lines 5 in this way, by cutting any of separable lines 5, 5, . . . , it is possible to select an optimum insertion position of the part B of the body periphery according to the difference in the size and shape of the part B of the body periphery such as a fingertip, a toe tip, or an ear periphery.

Figure 12:
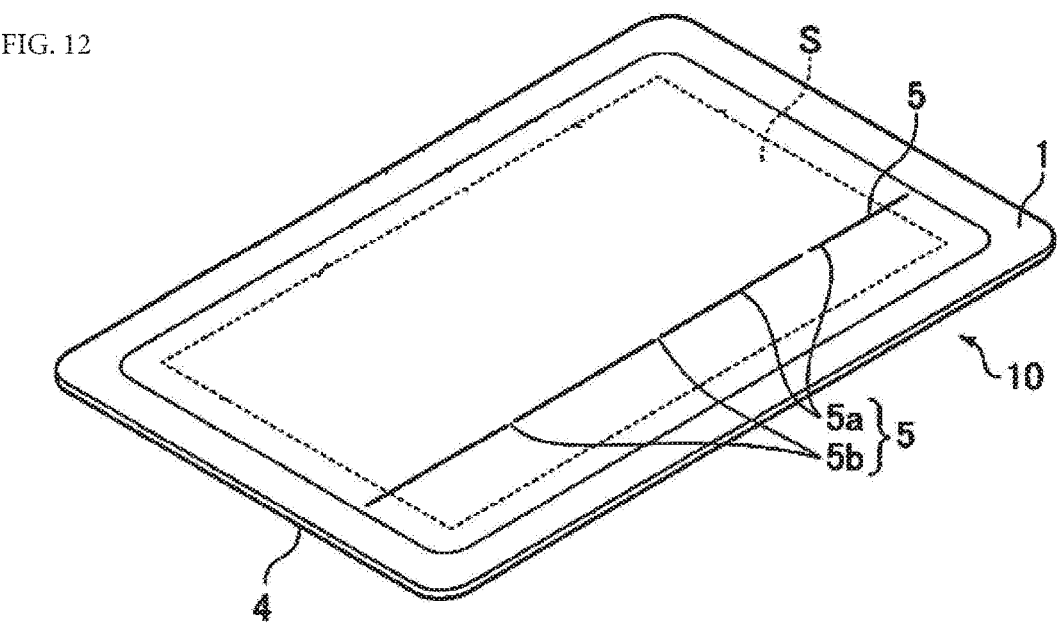
FIG. 12 is a perspective view of still another embodiment of a heating body of the present invention.
Figure 13:
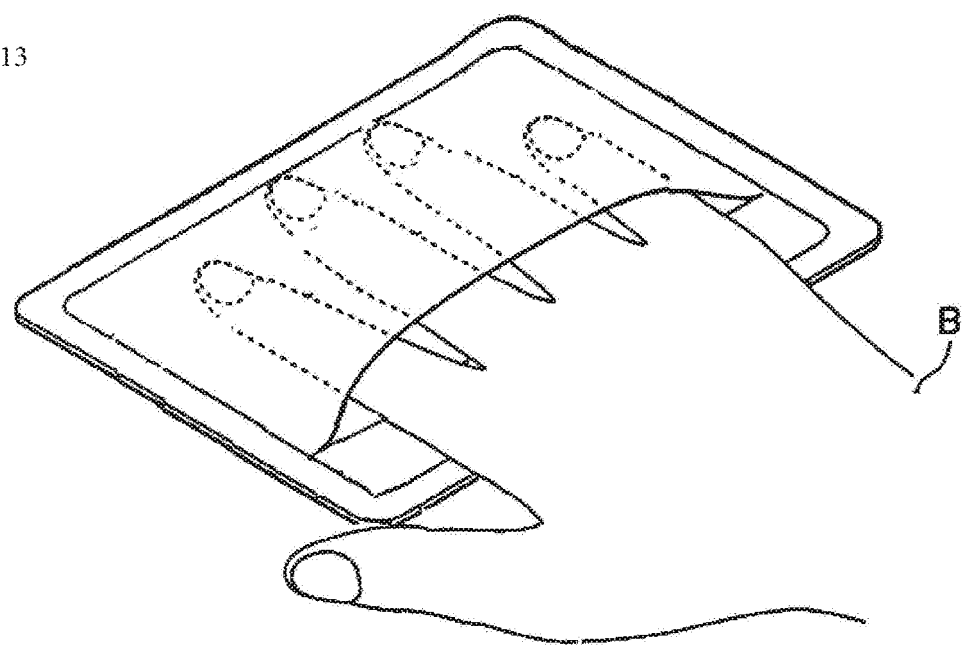
FIG. 13 is an explanatory diagram illustrating an example of use of the embodiment as illustrated in FIG. 12.

As illustrated in FIG. 12, the number of the separable lines 5 may be one. In this case, as illustrated in FIG. 13, the insertion space S forms a pocket during use, and the inserted body part B such as the hand can be effectively warmed.

The separable line 5 provided on the first base material 1 can be provided so as to extend in the longitudinal direction of the heating body 10, and in that case, the substantially center line having both ends on the short side and two of the plurality of separable lines 5, 5 are preferably provided so as to be substantially parallel. In addition, the shape of the separable line 5 can be selected as appropriate such as a perforation in which the cut portions 5a are provided at regular intervals, a perforation shaped like a series of reversed "V" in the vertical direction, a perforation in which staggered shapes are adjacent to each other, or a curved perforation.

Figure 14:
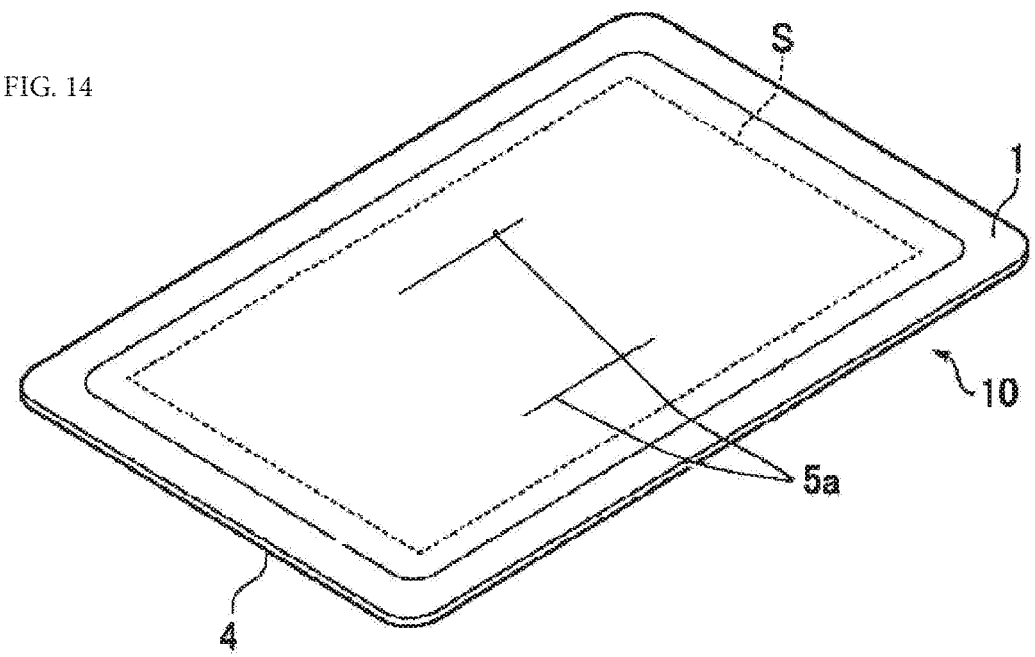
FIG. 14 is a perspective view of still another embodiment of a heating body of the present invention.
Figure 15:
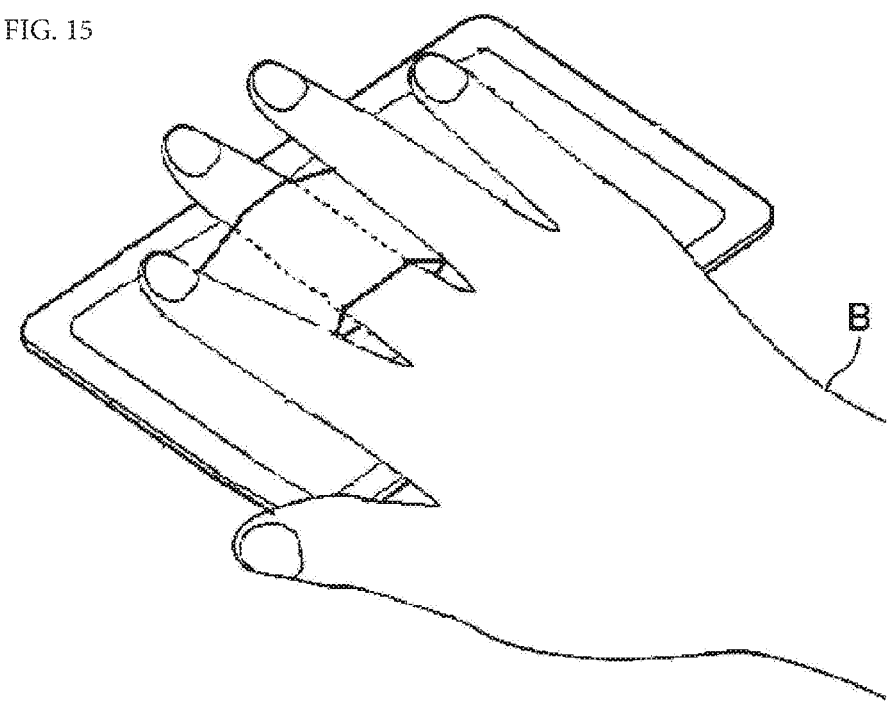
FIG. 15 is an explanatory diagram illustrating an example of use of the embodiment as illustrated in FIG. 14.
Figure 16:
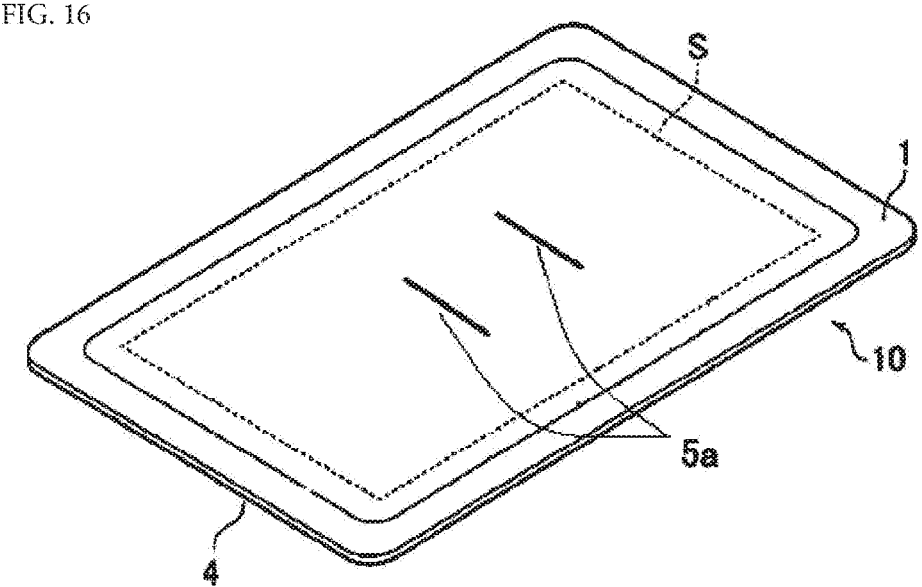
FIG. 16 is a perspective view of still another embodiment of a heating body of the present invention.
Figure 17:
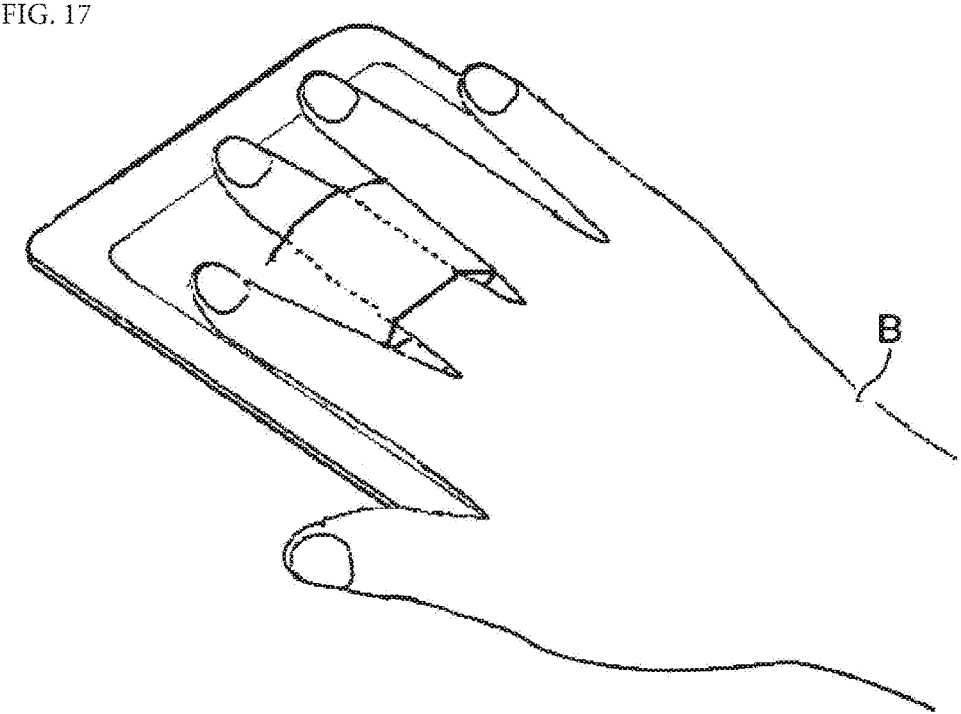
FIG. 17 is an explanatory diagram illustrating an example of use of the embodiment as illustrated in FIG. 16.

The length of the separable line, even when formed in the longitudinal direction of the heating body, can be appropriately determined according to the body part to be inserted. For example, as illustrated in FIGS. 14 and 15, in an embodiment used by inserting one finger, the length of the separable line may be shorter than the length of the long side. Similarly, the separable line can also be provided so as to extend in the short direction of the heating body 10. For example, the heating body 10 can be worn and used so that the long side is parallel to the finger by inserting one finger. Like that, the position, length, and the like of the separable line can be freely designed according to the purpose. The separable line may be a slit.

The size of the heating body 10 is not limited as long as the effect can be expected, and can be appropriately selected depending on the body part to be inserted. Assuming that the heating body 10 as illustrated in FIG. 1 is used by being worn on a hand, the size is preferably 30 to 150 mm in length and 50 to 250 mm in width.

In addition, the corners of the heating body 10 can be provided with an optional curve or roundness (R: radius) as necessary as in the drawings in order to alleviate or reduce the uncomfortable feeling in a case where they touch the skin while fixed to the body. In this case, R5 mm or more is preferable.

The first base material 1 and the second base material 2 are formed of a complex in which stretchable or non-stretchable first base material 1 is continuously bonded to a part of the second base material 2 which is a non-stretchable member. That is, a structure is adopted, in which a fusion layer is provided at least at a part of the periphery or the like of one surface of the first base material 1, and the second base material 2 is continuously bonded thereto through the fusion layer.

EXAMPLES

1. Production of Heating Body

Using each of the packaging materials described later as the first base material and the second base material, a heating body (warmer) was produced as follows. As a covering material, a material obtained by laminating a PET spunlace nonwoven fabric (basis weight of 30 g/m$^2$, produced by Shinwa Co., Ltd.) and a polyethylene-based film (thickness of 30 μm, produced by JAYFILM Co., Ltd.) by an extrusion lamination method with LDPE resin (thickness of 20 μm, produced by Japan polyethylene Corporation) was used. As a heat-generating composition, 22.5 g of a composition having a composition of 25.2 parts by weight of activated carbon, 3.3 parts by weight of water absorptive polymer, 0.6 parts by weight of sodium tripolyphosphate which is a pH adjuster, and 60.0 parts by weight of 8 wt % aqueous solution of sodium chloride which is a reaction accelerator, with respect to 100 parts by weight of iron powder, was used.

The respective base materials were arranged so that the heat-sealable resin layer of the first base material and the nonwoven fabric of the second base material were in contact with each other, and the first base material and the second base material were laminated by a curtain spray method using 1 g/m$^2$ of polyolefin-based hot-melt adhesive (Henkel Japan, Co., Ltd., "TECHNOMELT 34-601A") to prepare a one-surface side laminated base material. In this laminated base material, the first base material and the second base material are temporarily fixed, but are easily peeled off to form a space between both base materials.

The one-surface side laminated base material produced as described above and the covering material were set in a warmer producing machine so that the resin film layer of the second base material and the polyethylene-based film layer of the covering material face each other. The covering material were needle hole-processed in-line. The peripheral edge portion was heat-sealed at various temperatures with the warming machine at 5.74 m/min speed to produce rectangular warmers with a short side of 100 mm and a long side of 135 mm. The seal directions are a horizontal seal on the short side and a vertical seal on the long side, and the seal widths are 9 mm for the horizontal seal and 7 mm for the vertical seal.

Example 1

First Base Material

An mLLDPE resin (thickness of 20 μm, produced by Japan Polyethylene Corporation) was laminated to a PET spunlace nonwoven fabric (basis weight of 30 g/m², produced by Shinwa Co., Ltd.) by an extrusion lamination method. Thereafter, perforations (cut portion of 29.2 mm, non-cut portion of 0.6 mm) were made at both sides of the central portion of 50 mm width in the horizontal direction (short side) of 100 mm of a warmer.

Second Base Material

A PP spunbond nonwoven fabric (homo PP, melting point of 160° C.; basis weight of 18 g/m², produced by Shinwa Co., Ltd.) and a PE-based film (thickness of 30 μm, produced by JAYFILM Co., Ltd.) were laminated by an extrusion lamination method with an LDPE resin (thickness of 20 μm, produced by Tosoh Corporation).

Example 2

First Base Material

An mLLDPE resin (thickness of 20 μm, produced by Japan Polyethylene Corporation) was laminated to a PET spunlace nonwoven fabric (basis weight of 30 g/m², produced by Shinwa Co., Ltd.) by an extrusion lamination method. Thereafter, perforations (cut portion of 29.2 mm, non-cut portion of 0.6 mm) were made at both sides of the central portion of 50 mm width in the horizontal direction (short side) of 100 mm of a warmer.

Second Base Material

A flat-type PP/PE thermal bond nonwoven fabric (core of PP, sheath of HDPE, melting point of 137° C.; basis weight of 15 g/m², produced by Shinwa Co., Ltd.) and a PE-based film (thickness of 30 μm, produced by JAYFILM Co., Ltd.) were laminated by an extrusion lamination method with an LDPE resin (thickness of 20 μm, produced by Tosoh Corporation).

Example 3

First Base Material

An mLLDPE resin (thickness of 30 μm, produced by Japan Polyethylene Corporation) was laminated to a PET spunlace nonwoven fabric (basis weight of 30 g/m², produced by Shinwa Co., Ltd.) by an extrusion lamination method. Thereafter, perforations (cut portion of 29.2 mm, non-cut portion of 0.6 mm) were made at both sides of the central portion of 50 mm width in the horizontal direction (short side) of 100 mm of a warmer.

Second Base Material

An oven-type PP/PE thermal bond nonwoven fabric (core of PP, sheath of HDPE, melting point of 137° C.; basis weight of 25 g/m², produced by Shinwa Co., Ltd.) and a PE-based film (thickness of 30 μm, produced by JAYFILM Co., Ltd.) were laminated by an extrusion lamination method with an LDPE resin (thickness of 15 μm, produced by Tosoh Corporation).

Example 4

First Base Material

An mLLDPE resin (thickness of 30 μm, produced by Japan Polyethylene Corporation) was laminated to a PET spunlace nonwoven fabric (basis weight of 30 g/m², produced by Shinwa Co., Ltd.) by an extrusion lamination method. Thereafter, perforations (cut portion of 29.2 mm, non-cut portion of 0.6 mm) were made at both sides of the central portion of 50 mm width in the horizontal direction (short side) of 100 mm of a warmer.

Second Base Material

An oven-type PP/PE thermal bond nonwoven fabric (core of PP, sheath of HDPE, melting point of 137° C.; basis weight of 25 g/m², produced by Shinwa Co., Ltd.) and a PE-based film (thickness of 30 μm, produced by JAYFILM Co., Ltd.) were laminated by an extrusion lamination method with a mLLDPE resin (thickness of 15 μm, produced by Japan Polyethylene Corporation).

Example 5

First Base Material

An mLLDPE resin (thickness of 30 μm, produced by Japan Polyethylene Corporation) was laminated to a PET spunlace nonwoven fabric (basis weight of 30 g/m², produced by Shinwa Co., Ltd.) by an extrusion lamination method. Thereafter, perforations (cut portion of 29.2 mm, non-cut portion of 0.6 mm) were made at both sides of the central portion of 50 mm width in the horizontal direction (short side) of 100 mm of a warmer.

Second Base Material

A flat-type PP/PE thermal bond nonwoven fabric (core of PP, sheath of HDPE, melting point of 137° C.; basis weight of 25 g/m², produced by Shinwa Co., Ltd.) and a PE-based film (thickness of 30 μm, produced by JAYFILM Co., Ltd.) were laminated by an extrusion lamination method with an LDPE resin (thickness of 15 μm, produced by Tosoh Corporation).

Example 6

First Base Material

An mLLDPE resin (thickness of 30 μm, produced by Japan Polyethylene Corporation) was laminated to a PET spunlace nonwoven fabric (basis weight of 30 g/m², produced by Shinwa Co., Ltd.) by an extrusion lamination method. Thereafter, perforations (cut portion of 29.2 mm, non-cut portion of 0.6 mm) were made at both sides of the central portion of 50 mm width in the horizontal direction (short side) of 100 mm of a warmer.

Second Base Material

A flat-type PP/PE thermal bond nonwoven fabric (core of PP, sheath of HDPE, melting point of 137° C.; basis weight of 25 g/m², produced by Shinwa Co., Ltd.) and a PE-based film (thickness of 30 μm, produced by JAYFILM Co., Ltd.) were laminated by an extrusion lamination method with an mLLDPE resin (thickness of 15 μm, produced by Japan Polyethylene Corporation).

Example 7

First Base Material

A PET spunlace nonwoven fabric (basis weight of 30 g/m², produced by Shinwa Co., Ltd.) and a PE-based film (thickness of 30 μm) were laminated by an extrusion lamination method with an LDPE resin (thickness of 20 μm, produced by Japan Polyethylene Corporation). Thereafter, perforations (cut portion of 29.2 mm, non-cut portion of 0.6 mm) were made at both sides of the central portion of 50 mm width in the horizontal direction (short side) of 100 mm of a warmer.

Second Base Material

An oven-type PP/PE thermal bond nonwoven fabric (core of PP, sheath of HDPE, melting point of 137° C.; basis weight of 25 g/m², produced by Shinwa Co., Ltd.) and a PE-based film (thickness of 30 μm, produced by JAYFILM Co., Ltd.) were laminated by an extrusion lamination method with an LDPE resin (thickness of 20 μm, produced by Japan Polyethylene Corporation).

Example 8

First Base Material

An mLLDPE resin (thickness of 30 μm, 10% of milk white MB added, produced by Japan Polyethylene Corporation) was laminated to a PET spunlace nonwoven fabric (basis weight of 30 g/m², black back printing, produced by Shinwa Co., Ltd.) by an extrusion lamination method. Thereafter, perforations (cut portion of 29.2 mm, non-cut portion of 0.6 mm) were made at both sides of the central portion of 50 mm width in the horizontal direction (short side) of 100 mm of a warmer. Note that, "10% of milk white MB added" means that, with the mLLDPE amount as being 100%, an amount of the milk white master batch (MB) corresponding to 10% thereof was externally added. The milk white MB was produced by kneading 70% titanium oxide in advance with 30% of LDPE in order to improve the compatibility and dispersibility of milk white titanium oxide in mLLDPE, and cutting this kneaded resin from a heated extruder into pellets. Here, every "%" means percent by weight.

Second Base Material

An oven-type PP/PE thermal bond nonwoven fabric (core of PP, sheath of HDPE, melting point of 137° C.; basis weight of 25 g/m², produced by Shinwa Co., Ltd.) and a PE-based film (thickness of 30 μm, produced by JAYFILM Co., Ltd.) were laminated by a curtain spray method using a polyolefin-based hot melt adhesive.

Comparative Example 1

First Base Material

A PET spunlace nonwoven fabric (basis weight of 30 g/m², produced by Shinwa Co., Ltd.) and a PE-based film (thickness of 30 μm, produced by JAYFILM Co., Ltd.) were laminated by an extrusion lamination method with an LDPE resin (thickness of 20 μm, produced by Japan Polyethylene Corporation). Thereafter, perforations (cut portion of 29.2 mm, non-cut portion of 0.6 mm) were made at both sides of the central portion of 50 mm width in the horizontal direction (short side) of 100 mm of a warmer.

Second Base Material

A PET spunlace nonwoven fabric (PET, melting point of 255° C.; basis weight of 30 g/m², produced by Shinwa Co., Ltd.) and a PE-based film (thickness of 30 μm, produced by JAYFILM Co., Ltd.) were laminated by an extrusion lamination method with an LDPE resin (thickness of 20 μm, produced by Japan Polyethylene Corporation).

Comparative Example 2

First Base Material

A PET spunlace nonwoven fabric (basis weight of 30 g/m², produced by Shinwa Co., Ltd.) and a PE-based film (thickness of 30 μm, produced by JAYFILM Co., Ltd.) were laminated by an extrusion lamination method with an LDPE resin (thickness of 20 μm, produced by Japan Polyethylene Corporation). Thereafter, perforations (cut portion of 29.2 mm, non-cut portion of 0.6 mm) were made at both sides of the central portion of 50 mm width in the horizontal direction (short side) of 100 mm of a warmer.

Second Base Material

A PET spunlace nonwoven fabric (PET, melting point of 255° C.; basis weight of 30 g/m², produced by Shinwa Co., Ltd.) and a PE-based film (thickness of 30 μm, produced by JAYFILM Co., Ltd.) were laminated by an extrusion lamination method with an LDPE resin (thickness of 40 μm, produced by Japan Polyethylene Corporation).

Comparative Example 3

First Base Material

An mLLDPE resin (thickness of 30 μm, 10% of milk white MB added, produced by Japan Polyethylene Corporation) was laminated to a PET spunlace nonwoven fabric (basis weight of 30 g/m², black back printing, produced by Shinwa Co., Ltd.) by an extrusion lamination method. Thereafter, perforations (cut portion of 29.2 mm, non-cut portion of 0.6 mm) were made at both sides of the central portion of 50 mm width in the horizontal direction (short side) of 100 mm of a warmer.

Second Base Material

A PET spunlace nonwoven fabric (PET, melting point of 255° C.; basis weight of 30 g/m², produced by Shinwa Co., Ltd.) and a PE-based film (thickness of 30 μm, produced by JAYFILM Co., Ltd.) were laminated by an extrusion lamination method with an LDPE resin (thickness of 20 μm, produced by Japan Polyethylene Corporation).

Table 1 indicates a summary of each of the above base materials.

TABLE 1

| | | Example 1 | Example 2 | Example 3 | Example 4 | Example 5 | Example 6 | Example 7 |
|---|---|---|---|---|---|---|---|---|
| First base material | nonwoven fabric material/ | PET | PET | PET | PET | PET | PET | PET |
| | manufacturing method/ | spunlace | spunlace | spunlace | spunlace | spunlace | spunlace | spunlace |
| | basis weight (g/m²) | 30 | 30 | 30 | 30 | 30 | 30 | 30 |
| | resin/ manufacturing method/ thickness(μm) | — | — | — | — | — | — | LDPE Extrusion lamination 20 |
| | resin/ manufacturing | mLLDPE Extrusion | mLLDPE Extrusion | mLLDPE Extrusion | mLLDPE Extrusion | mLLDPE Extrusion | mLLDPE Extrusion | PE-based film |

TABLE 1-continued

| | | | | | | | | |
|---|---|---|---|---|---|---|---|---|
| Second base material | method/thickness(μm) | lamination 20 | lamination 20 | lamination 30 | lamination 30 | lamination 30 | lamination 30 | 30 |
| | nonwoven fabric material/ | PP | PP/PE(F) | PP/PE(O) | PP/PE(O) | PP/PE(F) | PP/PE(F) | PP/PE(O) |
| | manufacturing method/ | spunbond | thermal bond | thermal bond | thermal bond | thermal bond | thermal bond | thermal bond |
| | basis weight (g/m²) | 18 | 15 | 25 | 25 | 25 | 25 | 25 |
| | laminating resin/ | LDPE | LDPE | LDPE | LDPE | LDPE | LDPE | LDPE |
| | manufacturing method/ | Extrusion lamination | Extrusion lamination | Extrusion lamination | Extrusion lamination | Extrusion lamination | Extrusion lamination | Extrusion lamination |
| | thickness(μm) | 20 | 20 | 15 | 15 | 15 | 15 | 20 |
| | resin/ | PE-based film | PE-based film | PE-based film | PE-based film | PE-based film | PE-based film | PE-based film |
| | manufacturing method/ | | | | | | | |
| | thickness(μm) | 30 | 30 | 30 | 30 | 30 | 30 | 30 |

| | | Example 8 | Comparative Example 1 | Comparative Example 2 | Comparative Example 3 |
|---|---|---|---|---|---|
| First base material | nonwoven fabric material/ | PET | PET | PET | PET |
| | manufacturing method/ | spunlace | spunlace | spunlace | spunlace |
| | basis weight (g/m²) | 30(black back printing) | 30 | 30 | 30(black back printing) |
| | resin/ | — | LDPE | LDPE | — |
| | manufacturing method/ | | Extrusion lamination | Extrusion lamination | |
| | thickness(μm) | | 20 | 20 | |
| | resin/ | mLLDPE (milk white MB 10% added) | PE-based | PE-based | mLLDPE (milk white MB 10% added) |
| | manufacturing method/ | Extrusion lamination | film | film | Extrusion lamination |
| | thickness(μm) | 30 | 30 | 30 | 30 |
| Second base material | nonwoven fabric material/ | PP/PE(O) | PET | PET | PET |
| | manufacturing method/ | thermal bond | spunlace | spunlace | spunlace |
| | basis weight (g/m²) | 25 | 30 | 30 | 30 |
| | laminating resin/ | polyolefin-based hot melt adhesive | LDPE | LDPE | LDPE |
| | manufacturing method/ | Curtain spray lamination | Extrusion lamination | Extrusion lamination | Extrusion lamination |
| | thickness(μm) | 10 | 20 | 40 | 20 |
| | resin/ | PE-based film | PE-based film | PE-based film | PE-based film |
| | manufacturing method/ | | | | |
| | thickness(μm) | 30 | 30 | 30 | 30 |

F: Flat-type
O: Oven-type

2. Measurement of Heat Seal Strength

Seal strengths (between the first base material and the second base material, and between the second base material and the covering material) of the bag for accommodating a heat-generating composition produced as described above were measured using a tensile tester (produced by Aikoh Engineering Co., Ltd., MODEL 1301-D, 0113).

First, each of the sealed parts on the four sides of the rectangular bag was cut into a size of 15±0.5 mm×35±5 mm to prepare a sample. An upper limit adjustment ring screw was set so that a chucking interval of the tensile tester was 40±5 mm. The PEAK switch of the tester was pressed to turn on light of a lamp.

One end (5 to 10 mm) of the sample was inserted into an (upper) chucking part of the tester and the other end of the sample was inserted into a (lower) chucking part. The tensile speed was set to 300 (mm/min) and measurement was started. A measured MAX value was recorded when the sample broke or the tensile movement stopped.

The results are shown in Tables 2 and 3. In Tables 2 and 3, "n=1" and "n=2" for the seal strengths represent numbers assigned to respective sides of a rectangle that have been vertically or horizontally sealed.

TABLE 2

| Preset temperature of sealing rolls (° C.) | | Example 1 Seal strength(Kgf/15 mm) | | | | | | | | Example 2 Seal strength(Kgf/15 mm) | | | | | | | |
|---|---|---|---|---|---|---|---|---|---|---|---|---|---|---|---|---|---|
| | | between first base material and second base material | | | | between second base material and covering material | | | | between first base material and second base material | | | | between second base material and covering material | | | |
| covering material side | first base material side | horizontal seal | | vertical seal | | horizontal seal | | vertical seal | | horizontal seal | | vertical seal | | horizontal seal | | vertical seal | |
| | | n = 1 | n = 2 | n = 1 | n = 2 | n = 1 | n = 2 | n = 1 | n = 2 | n = 1 | n = 2 | n = 1 | n = 2 | n = 1 | n = 2 | n = 1 | n = 2 |
| 155 | 145 | 0.58 | 0.70 | 0.41 | 0.67 | 1.47 | 1.60 | 1.29 | 1.52 | 0.36 | 0.67 | 0.47 | 0.56 | 1.47 | 1.58 | 1.33 | 1.33 |
| 155 | 155 | 0.82 | 0.93 | 0.42 | 0.79 | 1.44 | 1.57 | 1.40 | 1.61 | 0.62 | 0.81 | 0.86 | 0.91 | 1.32 | 1.46 | 1.34 | 1.51 |
| 155 | 160 | 0.69 | 1.16 | 0.54 | 0.61 | 1.33 | 1.47 | 1.52 | 1.71 | 0.79 | 0.86 | 0.68 | 0.89 | 1.18 | 1.63 | 1.47 | 1.59 |
| 155 | 170 | 0.96 | 1.03 | 0.96 | 1.03 | 1.38 | 1.52 | 0.98 | 1.07 | 0.52 | 1.02 | 0.54 | 0.64 | 1.42 | 1.49 | 1.64 | 1.71 |

| Preset temperature of sealing rolls (° C.) | | Example 3 Seal strength(Kgf/15 mm) | | | | | | | | Example 4 Seal strength(Kgf/15 mm) | | | | | | | |
|---|---|---|---|---|---|---|---|---|---|---|---|---|---|---|---|---|---|
| | | between first base material and second base material | | | | between second base material and covering material | | | | between first base material and second base material | | | | between second base material and covering material | | | |
| covering material side | first base material side | horizontal seal | | vertical seal | | horizontal seal | | vertical seal | | horizontal seal | | vertical seal | | horizontal seal | | vertical seal | |
| | | n = 1 | n = 2 | n = 1 | n = 2 | n = 1 | n = 2 | n = 1 | n = 2 | n = 1 | n = 2 | n = 1 | n = 2 | n = 1 | n = 2 | n = 1 | n =2 |
| 155 | 145 | 1.16 | 1.30 | 1.35 | 1.54 | 1.44 | 1.65 | 1.13 | 1.28 | 0.88 | 1.03 | 1.26 | 1.36 | 1.46 | 1.68 | 1.16 | 1.36 |
| 155 | 150 | 1.03 | 1.08 | 1.28 | 1.37 | 1.40 | 1.47 | 1.27 | 1.38 | — | — | — | — | — | — | — | — |
| 155 | 155 | 1.12 | 1.35 | 1.43 | 1.47 | 1.50 | 1.51 | 1.39 | 1.40 | — | — | — | — | — | — | — | — |
| 155 | 165 | 1.20 | 1.26 | 1.39 | 1.54 | 1.42 | 1.67 | 1.32 | 1.35 | — | — | — | — | — | — | — | — |
| 155 | 175 | 1.43 | 1.59 | 1.39 | 1.54 | 1.55 | 1.76 | 1.34 | 1.52 | — | — | — | — | — | — | — | — |

| Preset temperature of sealing rolls (° C.) | | Example 5 Seal strength(Kgf/15 mm) | | | | | | | | Example 6 Seal strength(Kgf/15 mm) | | | | | | | |
|---|---|---|---|---|---|---|---|---|---|---|---|---|---|---|---|---|---|
| | | between first base material and second base material | | | | between second base material and covering material | | | | between first base material and second base material | | | | between second base material and covering material | | | |
| covering material side | first base material side | horizontal seal | | vertical seal | | horizontal seal | | vertical seal | | horizontal seal | | vertical seal | | horizontal seal | | vertical seal | |
| | | n = 1 | n = 2 | n = 1 | n = 2 | n = 1 | n = 2 | n = 1 | n = 2 | n = 1 | n = 2 | n = 1 | n = 2 | n = 1 | n = 2 | n = 1 | n = 2 |
| 155 | 145 | 0.86 | 1.03 | 1.80 | 1.81 | 1.51 | 1.67 | 1.41 | 1.56 | 0.90 | 0.96 | 1.45 | 1.52 | 1.42 | 1.57 | 1.40 | 1.47 |
| 155 | 150 | 0.85 | 1.29 | 1.32 | 1.57 | 1.50 | 1.66 | 1.24 | 1.60 | — | — | — | — | — | — | — | — |
| 155 | 155 | 0.78 | 1.69 | 1.52 | 1.95 | 1.55 | 1.95 | 1.12 | 1.50 | — | — | — | — | — | — | — | — |
| 155 | 165 | 1.13 | 1.28 | 1.49 | 1.52 | 1.42 | 1.45 | 1.51 | 1.51 | — | — | — | — | — | — | — | — |
| 155 | 175 | 1.26 | 1.71 | 1.81 | 2.00 | 1.37 | 1.62 | 1.49 | 1.74 | — | — | — | — | — | — | — | — |

| Preset temperature of sealing rolls (° C.) | | Example 7 Seal strength(Kgf/15 mm) | | | | | | | | Example 8 Seal strength(Kgf/15 mm) | | | | | | | |
|---|---|---|---|---|---|---|---|---|---|---|---|---|---|---|---|---|---|
| | | between first base material and second base material | | | | between second base material and covering material | | | | between first base material and second base material | | | | between second base material and covering material | | | |
| covering material side | first base material side | horizontal seal | | vertical seal | | horizontal seal | | vertical seal | | horizontal seal | | vertical seal | | horizontal seal | | vertical seal | |
| | | n = 1 | n = 2 | n = 1 | n = 2 | n = 1 | n = 2 | n = 1 | n = 2 | n = 1 | n = 2 | n = 1 | n = 2 | n = 1 | n = 2 | n = 1 | n = 2 |
| 155 | 145 | 0.05 | 0.06 | 0.62 | 0.77 | 2.04 | 2.04 | 1.32 | 1.47 | 0.22 | 0.40 | 0.97 | 1.20 | 1.27 | 1.48 | 0.96 | 1.11 |
| 155 | 150 | 0.13 | 0.15 | 1.22 | 1.25 | 1.96 | 2.03 | 1.47 | 1.51 | 0.85 | 1.12 | 1.14 | 1.31 | 1.35 | 1.36 | 1.21 | 1.32 |
| 155 | 155 | 0.54 | 0.56 | 1.46 | 1.54 | 1.62 | 1.74 | 1.45 | 1.54 | 1.16 | 1.25 | 1.20 | 1.32 | 1.29 | 1.50 | 1.10 | 1.22 |
| 155 | 165 | 0.64 | 1.00 | 1.15 | 1.66 | 1.73 | 1.81 | 1.50 | 1.57 | 1.33 | 1.43 | 1.20 | 1.23 | 1.29 | 1.56 | 1.06 | 1.18 |
| 155 | 175 | 0.75 | 1.07 | 1.33 | 1.55 | 1.78 | 1.94 | 1.38 | 1.56 | 1.80 | 1.90 | 1.32 | 1.34 | 1.47 | 1.62 | 1.18 | 1.25 |

TABLE 3

| Preset temperature of sealing rolls (° C.) | | Comparative Example 1 Seal strength(Kgf/15 mm) | | | | | | | | Comparative Example 2 Seal strength(Kgf/15 mm) | | | | | | | |
|---|---|---|---|---|---|---|---|---|---|---|---|---|---|---|---|---|---|
| | | between first base material and second base material | | | | between second base material and covering material | | | | between first base material and second base material | | | | between second base material and covering material | | | |
| covering material side | first base material side | horizontal seal | | vertical seal | | horizontal seal | | vertical seal | | horizontal seal | | vertical seal | | horizontal seal | | vertical seal | |
| | | n = 1 | n = 2 | n = 1 | n = 2 | n = 1 | n = 2 | n = 1 | n = 2 | n = 1 | n = 2 | n = 1 | n = 2 | n = 1 | n = 2 | n = 1 | n = 2 |
| 165 | 170 | 0.18 | 0.40 | 0.54 | 0.80 | 1.45 | 1.50 | 1.47 | 1.79 | — | — | — | — | — | — | — | — |
| 170 | 175 | 0.13 | 0.17 | 0.84 | 1.10 | 1.49 | 1.57 | 1.25 | 2.09 | 0.43 | 0.51 | 2.16 | 2.31 | 1.13 | 1.73 | 1.04 | 1.08 |
| 175 | 180 | 0.10 | 0.39 | 0.63 | 1.29 | 1.54 | 1.80 | 1.44 | 1.57 | — | — | — | — | — | — | — | — |
| 185 | 185 | 0.20 | 0.50 | 1.32 | 1.39 | 1.55 | 2.05 | 1.43 | 1.83 | — | — | — | — | — | — | — | — |
| 200 | 200 | 0.37 | 0.82 | 1.55 | 1.86 | 1.61 | 1.88 | 1.83 | 2.03 | — | — | — | — | — | — | — | — |

| Preset temperature of sealing rolls (° C.) | | Comparative Example 3 Seal strength(Kgf/15 mm) | | | | | | | |
|---|---|---|---|---|---|---|---|---|---|
| | | between first base material and second base material | | | | between second base material and covering material | | | |
| covering material side | first base material side | horizontal seal | | vertical seal | | horizontal seal | | vertical seal | |
| | | n = 1 | n = 2 | n = 1 | n = 2 | n = 1 | n = 2 | n = 1 | n = 2 |
| 155 | 145 | 0.32 | 0.65 | 0.78 | 1.01 | 1.48 | 1.49 | 0.94 | 1.22 |
| 155 | 150 | 0.33 | 0.39 | 0.79 | 0.86 | 1.43 | 1.76 | 1.28 | 1.64 |
| 155 | 155 | 0.30 | 0.59 | 0.86 | 1.25 | 1.74 | 2.06 | 1.87 | 1.91 |
| 155 | 165 | 0.56 | 0.70 | 0.89 | 0.93 | 1.80 | 1.95 | 1.44 | 1.45 |
| 155 | 175 | 0.69 | 0.80 | 1.13 | 1.23 | 1.34 | 1.50 | 1.38 | 1.38 |

In Examples 1 to 8, despite the heat sealing by the warmer-producing machine at a relatively low temperature and for an extremely short time, both of the vertical seals and the horizontal seals exhibited high seal strengths both of between the first base material and the second base material and between the second base material and the covering material. On the other hand, in Comparative Examples 1 to 3, even if the seal temperature was elevated, comparable high bonding strengths were not obtained on all four sides.

REFERENCE SIGNS LIST

1 First base material
1a Nonwoven fabric
1b Heat sealing layer
2 Second base material
2a Nonwoven fabric
2b Extruded laminate layer
2c Heat sealing layer
3 Heat-generating composition
4 Covering material
4a Nonwoven fabric
4b Heat sealing layer
5 Separable line
5a Cut portion (slit)
5b Non-cut portion
6 Opening
7 Belt-like portion
10 Heating body
B Peripheral part of the body (fingertip)
H Heat-generating portion
S Insertion space This application is based on Japanese Patent Application No. 2017-117578 filed on Jun. 15, 2017, and the contents described in the specification and claims of Japanese Patent Application No. 2017-117578 are all incorporated in this application specification.

The invention claimed is:

1. A heating body in which a heat-generating composition that generates heat by reacting with air is accommodated in a bag body formed by heat sealing a one-surface side laminated base material comprising a first base material and a second base material, and a covering material, at a peripheral edge portion thereof, characterized in that:
the first base material has one surface being a nonwoven fabric layer and an other surface being a heat sealable resin layer;
the second base material is a sheet in which an olefin-based nonwoven fabric layer and a resin film are laminated using an olefin-based resin that forms a laminate layer between the olefin-based nonwoven fabric layer and the resin film;
the first base material and the second base material are capable of forming a space into which a body part can be inserted or held, in a part surrounded by the peripheral edge portion; and
in a heat sealed part of the bag body peripheral edge portion, the heat sealable resin layer of the first base material and the nonwoven fabric layer of the second base material are bonded together, and the resin film of the second base material and the covering material are bonded together.

2. The heating body according to claim 1, wherein the resin constituting the olefin-based nonwoven fabric layer of the second base material has a melting point of 130° C. or higher and 160° ° C. or lower.

3. The heating body according to claim 1, wherein both of a bonding strength between the first base material and the second base material and a bonding strength between the second base material and the covering material are 0.75 kgf/15 mm or more in four locations of the peripheral edge portion of the heating body.

4. The heating body according to claim 1, wherein the first base material is provided with at least one slit or a separable line.

5. The heating body according to claim 4, wherein the separable line has a straight line or a wavy line perforation.

* * * * *